US006492112B1

(12) United States Patent
Reinhard et al.

(10) Patent No.: US 6,492,112 B1
(45) Date of Patent: Dec. 10, 2002

(54) MITOGEN-ACTIVATED PROTEIN KINASE KINASE 7 (MKK7)

(75) Inventors: Christoph Reinhard, Alameda, CA (US); Altaf Kassam, Oakland, CA (US); David Pot, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/206,166

(22) Filed: Dec. 7, 1998

Related U.S. Application Data

(60) Provisional application No. 60/070,114, filed on Dec. 31, 1997.

(51) Int. Cl.[7] .............................. C12Q 1/48; C12Q 1/68; C12N 1/20; C12N 9/12; C12N 15/00
(52) U.S. Cl. ........................ 435/6; 435/15; 435/252.3; 435/320.1; 435/194; 435/7.4
(58) Field of Search ..................... 435/15, 194, 320.1, 435/252.3, 6

(56) References Cited

U.S. PATENT DOCUMENTS 6,136,596 A * 11/2000 Davis et al. ................. 435/325

FOREIGN PATENT DOCUMENTS

| WO | WO 96/36642 | 11/1996 |
| WO | WO 99/02547 | 1/1999 |
| WO | WO 99/09181 | 2/1999 |

OTHER PUBLICATIONS

Lawler et al., "SKK4, a novel activator of stress–activated protein kinase–1 (SAPK1/JNK)," *FEBS Letters* 414: 153–158, 1997.
Liu et al., "Three distinct signalling responses by murine fibroblasts to genotoxic stress," *Nature* 384: 273–276, 1996.
Lu et al., "Identification of c–Jun $NH_2$–terminal Protein Kinase (JNK)–activating Kinase 2 as an Activator of JNK but Not p38," *The Journal of Biological Chemistry* 272(40): 24751–24754, 1997.
Tournier et al., "Mitogen–activated protein kinase kinase 7 is an activator of the c–Jun $NH_2$–terminal kinase," *Proc. Natl. Acad. Sci. USA* 94:7337–7342, 1997.
Wu et al., "Molecular Cloning and Characterization of Human JNKK2, a Novel Jun $NH_2$–Terminal Kinase–Specific Kinase," *Molecular and Cellular Biology* 17(12):7407–7416, 1997.
Yang et al., "Moleuclar cloning and characterization of human protein kinase that specifically activates c–Jun N–terminal kinase," *Gene* 212: 95–102, 1998.
Canman and Kastan, "Three paths to stress relief," *Nature* 384:213–214, 1996.
Foltz et al., "Human Mitogen–activated Protein Kinase Kinase 7 (MKK7) Is a Highly Conserved c–Jun N–terminal Kinase/Stress–activated Protein Kinase (JNK/SAPK) Activated by Environmental Stresses and Physiological Stimuli," *The Journal of Biological Chemistry* 273(15): 9344–9351, 1998.
Holland et al., "MKK7 Is a Stress–activated Mitogen–activated Protein Kinase Kinase Functionally Related to hemipterous," *The Journal of Biological Chemistry* 272(40): 24994–24998, 1997.

* cited by examiner

Primary Examiner—M. Monshipouri
(74) Attorney, Agent, or Firm—Jane E. R. Potter; Kimberlin L. Morley; Robert P. Blackburn

(57) ABSTRACT

A human gene encoding a novel mitogen-activated (MAP) kinase kinase, MKK7, provides methods and reagents for treating a variety of MKK7-mediated disorders, such as ischemic heart disease, kidney failure, oxidative liver damage, respiratory distress syndrome, heat and radiation burns, septic shock, autoimmune disorders, and inflammatory diseases. MKK7 reagents can also be used to induce or prevent apoptosis.

4 Claims, 11 Drawing Sheets

```
                                20                   40                    60
               AGGCCAAGAATTCGGCACGAGGCTTGATTTGCATGCAACACCCACAAAAAGGAAACACAC
H85962 ▶       AGGCCAAGAATTCGGCACGAGGCTTGATTTGCATGCAACACCCACAAAAAGGAAACACAC
MKK7.cds ◀
AA194047 ◀

80                  100                   120
               CCCCTCCTGCTCTGGCCACCCCAGCAGGCTCCGGGGGGCACCTGGCCTGGGTCCCCGGTG
H85962 ▶       CCCCTCCTGCTCTGGCCACCCCAGCAGGCTCCGGGGGGCACCTGGCCTGGGTCCCCGGTG
MKK7.cds ◀
AA194047 ◀

140                  160                   180
               CACTCACCCGGTCCTTCCCAGTCCTGGACCTCAACGTGGACTGGGCCAGGTGTGGGTGAG
H85962 ▶       CACTCACCCGGTCCTTCCCAGTCCTGGACCTCAACGTGGACTGGGCCAGGTGTGGGTGAG
MKK7.cds ◀
AA194047 ◀

200                  220                   240
               TGGAGGGACGGCCAGGGGCACGATGGGAGTGACCACCTCGCACCCCCACCCTCAGCCCGG
H85962 ▶       TGGAGGGACGGCCAGGGGCACGATGGGAGTGACCACCTCGCACCCCCACCCTCAGCCCGG
MKK7.cds ◀
AA194047 ◀

260                  280                   300
               CCCCCACCCCTGCTGGAGCTTGTCACACGTCCTCAAACCCCCACATCCACTCCCTCTGCC
H85962 ▶       CCCCCACCCCTGCTGGAGCTTGTCACACGTCCTCAAACCCCCACATCCACTCCCTCTGCC
MKK7.cds ◀
AA194047 ◀

320                  340                   360
               CTCCATCCCTGACTCCCTCCGGACCCCTCCCTTGGCCCCCGCTCCGTCACCGATTCCCTC
H85962 ▶       CTCCATCCCTGACTCCCTCCGGACCCCTCCCTTGGCCCCCGCTCCGTCACCGATTCCCTC
MKK7.cds ◀
AA194047 ◀

380                  400                   420
               CGGTCACCTGCTCTGCACCATGCCCCAAGACCACCTTCCCTGAAGGCCATCCTGTGCGGC
H85962 ▶       CGGTCACCTGCTCTGCACCATGCCCCAAGACCACCTTCCCTGAAGGCCATCCTGTGCGGC
MKK7.cds ◀
AA194047 ◀
```

*Fig. 1A*

```
                           440            460            480
             CAGGGCCCCGCAGACCCCTCCACATCCCCTGAGGTCTTCAACTCACCCCAAGCTGTGGCC
H85962 ▶     CAGGGCCCCGCAGACCCCTCCACATCCCCTGAGGTCTTCAACTCACCCCAAGCTGTGGCC
MKK7.cds ◀
AA194047 ◀

500            520            540
             CCCGGAGACCCCAGAGCAGCAGCCCCAGCCCAGCTCCCCAGTGCCCGAGGGCGGTTGGGG
H85962 ▶     CCCGGAGACCCCAGAGCAGCAGCCCCAGCCCAGCTCCCCAGTGCCCGAGGGCGGTTGGGG
MKK7.cds ◀
AA194047 ◀

560            580            600
             CCCCACCACAAGCAGCTAATCGTGACTTTGGTAAAAGTTTCTGAAGGTACCGACAACCCC
H85962 ▶     CCCCACCACAAGCAGCTAATCGTGACTTTGGTAAAAGTTTCTGAAGGTACCGACAACCCC
MKK7.cds ◀
AA194047 ◀

620            640            660
             ACGAGAACAAGCTCTCCTCCGCCCCCACCCCAAACACCCCACCAAGTACAATAAAATACA
H85962 ▶     ACGAGAACAAGCTCTCCTCCGCCCCCACCCCAAACACCCCACCAAGTACAATAAAATACA
MKK7.cds ◀
AA194047 ◀

680            700            720
             ATAAACTCCAAAAAGGACCCCCTGAGATCAAAGAGAGAGAGAGAGAGAGAGAGAGAGCGC
H85962 ▶     ATAAACTCCAAAAAGGACCCCCTGAGATCAAAGAGAGAGAGAGAGAGAGAGAGAGAGCGC
MKK7.cds ◀
AA194047 ◀

740            760            780
             GAGCGCGCAGCCCCGTCCAGCCGCAGTGGCAATGCCCACACTGCCTGGCTGGGGGCCACT
H85962 ▶     GAGCGCGCAGCCCCGTCCAGCCGCAGTGGCAATGCCCACACTGCCTGGCTGGGGGCCACT
MKK7.cds ◀
AA194047 ◀

800            820            840
             GACTCATTGCGCCATGGGAGACCTATGCAGACCCAGGGGACCCGTCAGGAGGTGGCTGGG
H85962 ▶     GACTCATTGCGCCATGGGAGACCTATGCAGACCCAGGGGACCCGTCAGGAGGTGGCTGGG
MKK7.cds ◀
AA194047 ◀
```

*Fig. 1B*

```
                              860              880              900
                    CCCAGGCTCAGGCCAGAAGAGAGACAGAGGCAGGGAGGGTGACGGGAGAGCCAGACAAGG
          H85962 ▶  CCCAGGCTCAGGCCAGAAGAGAGACAGAGGCAGGGAGGGTGACGGGAGAGCCAGACAAGG
          MKK7.cds ◀
          AA194047 ◀

920              940              960
                    ACAGAGAGGTAGAGCAGGGGACAGAGGGCGACGGAAGAGGAACGGGCGCGTGGGAGTGGC
          H85962 ▶  ACAGAGAGGTAGAGCAGGGGACAGAGGGCGACGGAAGAGGAACGGGCGCGTGGGAGTGGC
          MKK7.cds ◀
          AA194047 ◀

980              1000             1020
                    GAAGGACACAGCACGCTGGGAGCGTGCATGGTGGCTGCGGGACTCCAGGGCTCTCTCCTG
          H85962 ▶  GAAGGACACAGCACGCTGGGAGCGTGCATGGTGGCTGCGGGACTCCAGGGCTCTCTCCTG
          MKK7.cds ◀
          AA194047 ◀

1040             1060             1080
                    GCCCCTGGGGGCCGCCCCGGCCCAGAGGCTGCGGCTGAATGAACAGCGA...CTCTGATCG
          H85962 ▶  GCCCCTGGGGGCCGCCCCGGCCCAGAGGCTGCGGCTGAATGAACAGCGA..CTCTGATCG
          MKK7.cds ◀
          AA194047 ◀

1100             1120             1140
                    CGGCCTGCTGTCTTCCGTTCACAGTGTCTGTCGGGGGACGCACACGGCCGGCTGACCCCG
          H85962 ▶  CGGCCTGCTGTCTTCCGTTCACAGTGTCTGTCGGGGGACGCACACGGCCGGCTGACCCCG
          MKK7.cds ◀
          AA194047 ◀

1160             1180             1200
                    GGGTGGGAAGGGCGGGGGGGGTGGGTGGGCACCCCCCACTCTCTGTCCTCAGTCCTAGGT
          H85962 ▶  GGGTGGGAAGGGCGGGGGGGGTGGGTGGGCACCCCCCACTCTCTGTCCTCAGTCCTAGGT
          MKK7.cds ◀
          AA194047 ◀

1220             1240             1260
                    GGCCGTCC.AGGTCC.CAGGTC....TCCCCTGGCAGGCAGCTGGGTGGCCAAGTGGGGA
          H85962 ▶  GGCCGTCC.AGGTCC.CAGGTC....TCCCCTGGCAGGCAGCTGGGTGGCCAAGTGGGGA
          MKK7.cds ◀
          AA194047 ◀
```

*Fig. 1C*

```
                         1280           1300           1320
            GGGGGGCCTGTGGCCATGCCCCTGGCCCCCTGTGGGGCTGGCCGCC..............
H85962 ▶    GGGGGGCCTGTGGCCATGCCCCTGGCCCCCTGTGGGGCTGGCCGCC..............
MKK7.cds ◀
AA194047 ◀

1340           1360           1380
            ........GCCAAGCAGCTACCTGAAGAAGGGCAGGTGGGGCTGGCTCAGGACGCCGCTA
H85962 ▶    ........GCCAAGCAGCTACCTGAAGAAGGGCAGGTGGGGCTGGCTCAGGACGCCGCTA
MKK7.cds ◀                  CTACCTGAAGAAGGGCAGGTGGGGCTGGCTCAGGACGCCGCTA
AA194047 ◀

1400           1420           1440
            GTCCGCGGTGACTCAGTCTTCGCCATGACATCCTTGAACCAGGACGCCACGTCCACCTCC
H85962 ▶    GTCCGCGGTGACTCAGTCTTCGCCATGACATCCTTGAACCAGGACGCCACGTCCACCTCC
MKK7.cds ◀  GTCCGCGGTGACTCAGTCTTCGCCATGACATCCTTGAACCAGGACGCCACGTCCACCTCC
AA194047 ◀

1460           1480           1500
            AG.CGTCTCGTAGCGCTTGATGAAGCTGTGTTCAAGTAGCTTATTATACTTTGGTCTCTT
H85962 ▶    AG.CGTCTCGTAGCGCTTGATGAAGCTGTGTTCAAGTAGCTTATTATACTTTGGTCTCTT
MKK7.cds ◀  AG.CGTCTCGTAGCGCTTGATGAAGCTGTGTTCAAGTAGCTTATTATACTTTGGTCTCTT
AA194047 ◀

1520           1540           1560
            CCTGTGATCTTTAGTAAGGCAGTCTTTGACGAAGGACTGGAAGTCCCCCGAGAAGCCCAT
H85962 ▶    CCTGTGATCTTTAGTAAGGCAGTCTTTGACGAAGGACTGGAAGTCCCCCGAGAAGCCCAT
MKK7.cds ◀  CCTGTGATCTTTAGTAAGGCAGTCTTTGACGAAGGACTGGAAGTCCCCCGAGAAGCCCAT
AA194047 ◀

1580           1600           1620
            GTGTCCGGGCAGAAGCGGGGGCTCTTCCTGTAGGACTTTGGTGAGGACCTCAAAGTCCGT
H85962 ▶    GTGTCCGGGCAGAAGCGGGGGCTCTTCCTGTAGGACTTTGGTGAGGACCTCAAAGTCCGT
MKK7.cds ◀  GTGTCCGGGCAGAAGCGGGGGCTCTTCCTGTAGGACTTTGGTGAGGACCTCAAAGTCCGT
AA194047 ◀

1640           1660           1680
            CTTGCAGTTCTTGTAGGGAAACTGTCCTGTTGCCAGCTCCACCAACGAGATGCCCAGGCT
H85962 ▶    CTTGCAGTTCTTGTAGGGAAACTGTCCTGTTGCCAGCTCCACCAACGAGATGCCCAGGCT
MKK7.cds ◀  CTTGCAGTTCTTGTAGGGAAACTGTCCTGTTGCCAGCTCCACCAACGAGATGCCCAGGCT
AA194047 ◀
```

*Fig. 1D*

```
                    1700           1720            1740
           CCATACGTCGGCCCGGATGTCATAGTCCGGCTTGGTGGGGTCTGGGGGGTCAATGCGCTC
H85962 ▸   CCATACGTCGGCCCGGATGTCATAGTCCGGCTTGGTGGGGTCTGGGGGGTCAATGCGCTC
MKK7.cds ◂ CCATACGTCGGCCCGGATGTCATAGTCCGGCTTGGTGGGGTCTGGGGGGTCAATGCGCTC
AA194047 ◂

1760           1780            1800
           GGGTGCCATGTAGGCGGCACAGCCGGCGCTCCGCGTCTTGGCTTTGGAGTCCACCANGCG
H85962 ▸   GGGTGCCATGTAGGCGGCACAGCCGGCGCTCCGCGTCTTGGCTTTGGAGTCCACCAGGCG
MKK7.cds ◂ GGGTGCCATGTAGGCGGCACAGCCGGCGCTCCGCGTCTTGGCTTTGGAGTCCACCAGGCG
AA194047 ◂                                                          .GCG  ⎤
                                                                         |
                    1820           1840            1860                  |  OVERLAP
           GCCGCTGATGCCGAAGTCGCAGAGCTTGATCTGGCCCCGCTCGTCCAGCAGGATGTTGGA  |
H85962 ▸   GCCGC                                                         |
MKK7.cds ◂ GCCGCTGATGCCGAAGTCGCAGAGCTTGATCTGGCCCCGCTCGTCCAGCAGGATGTTGGA  |
AA194047 ◂ GCCGCTGATGCCGAAGTCGCAGAGCTTGATCTGGCCCCGCTCGTCCAGCAGGATGTTGGA  ⎦

1880           1900            1920
           GGGCTTGACGTCGCGGTGGATGACACCGTGCTTCTCCTTCAGGTAGTACAGCGCCTTCAC
H85962 ▸
MKK7.cds ◂ GGGCTTGACGTCGCGGTGGATGACACCGTGCTTCTCCTTCAGGTAGTACAGCGCCTTCAC
AA194047 ◂ GGGCTTGACGTCGCGGTGGATGACACCGTGCTTCTCCTTCAGGTAGTACAGCGCCTTCAC 1940           1960            1980
           AATCGCCACTGTCATCTTGCCCAGAATGCGCTCGGGGATGGGGCCCTGCATCCGCTTCTT
H85962 ▸
MKK7.cds ◂ AATCGCCACTGTCATCTTGCCCAGAATGCGCTCGGGGATGGGGCCCTGCATCCGCTTCTT
AA194047 ◂ AATCGCCACTGTCATCTTGCCCAGAATGCGCTCGGGGATGGGGCCCTGCATCCGCTTCTT 2000           2020            2040
           GAGCTTCTCAGCGCAGGTGCCCATGAGCTCCATGGCGATGAAGACGTCCGTGTTGGTGAT
H85962 ▸
MKK7.cds ◂ GAGCTTCTCAGCGCAGGTGCCCATGAGCTCCATGGCGATGAAGACGTCCGTGTTGGTGAT
AA194047 ◂ GAGCTTCTCAGCGCAGGTGCCCATGAGCTCCATGGCGATGAAGACGTCCGTGTTGGTGAT 2060           2080            2100
           GAACGTCCCAAAGCACTGCACGATGTAGGGGCAGTCGTGGCTCTTCAGCACCACATCCAG
H85962 ▸
MKK7.cds ◂ GAACGTCCCAAAGCACTGCACGATGTAGGGGCAGTCGTGGCTCTTCAGCACCACATCCAG
AA194047 ◂ GAACGTCCCAAAGCACTGCACGATGTAGGGGCAGTCGTGGCTCTTCAGCACCACATCCAG
```

*Fig. 1E*

```
                         2120              2140              2160
            GTCCATGAGGATGCGCTTGTTCTCCTCCTTGTTCCCGGAGCGCCGCATTTGCTTAACGGC
H85962▸
MKK7.cds◂   GTCCATGAGGATGCGCTTGTTCTCCTCCTTGTTCCCGGAGCGCCGCATTTGCTTAACGGC
AA194047◂   GTCCATGAGGATGCGCTTGTTCTCCTCCTTGTTCCCGGAGCGCCGCATTTGCTTAACGGC 2180              2200              2220
            AATGACGTGGCCGGTCTTCCGGAAGCGCATCTTCCACACCTGGCCGCAGGTGCCGCTGCC
H85962▸
MKK7.cds◂   AATGACGTGGCCGGTCTTCCGGAAGCGCATCTTCCACACCTGGCCGCAGGTGCCGCTGCC
AA194047◂   AATGACGTGGCCGGTCTTCCGGAAGCGCATCTTCCACACCTGGCCGCAGGTGCCGCTGCC 2240              2260              2280
            CATCTCGCCCAAGTTCTCCAGGTCGTTGATTTCTGCCTGGTAGCGCTGGCCCCCGATGGT
H85962▸
MKK7.cds◂   CATCTCGCCCAAGTTCTCCAGGTCGTTGATTTCTGCCTGGTAGCGCTGGCCCCCGATGGT
AA194047◂   CATCTCGCCCAAGTTCTCCAGGTCGTTGATTTCTGCCTGGTAGCGCTGGCCCCCGATGGT 2300              2320              2340
            CAGGTAGCCCGTCTGCTTCATGATCTCCTGCAGCTTCTGGTCAATCTCAATGCTCTCCAT
H85962▸
MKK7.cds◂   CAGGTAGCCCGTCTGCTTCATGATCTCCTGCAGCTTCTGGTCAATCTCAATGCTCTCCAT
AA194047◂   CAGGTAGCCCGTCTGCTTCATGATCTCCTGCAGCTTCTGGTCAATCTCAATGCTCTCCAT 2360              2380              2400
            GCTGCGGGGTGTGAACAGGGTTGACGGGAGCCCCAGCATGTGGCGGGGCCGGGCGGGGGG
H85962▸
MKK7.cds◂   GCTGCGGGGTGTGAACAGGGTTGACGGGAGCCCCAGCATGTGGCGGGGCCGGGCGGGGGG
AA194047◂   GCTGCGGGGTGTGAACAGGGTTGACGGGAGCCCCAGCATGTGGCGGGGCCGGGCGGGGGG 2420              2440              2460
            CGTGGGGTGCTGCGGGGAGCTCTCTGAGGATGGCGAGCGGCTGCCCCCATCGTTGGCCAG
H85962▸
MKK7.cds◂   CGTGGGGTGCTGCGGGGAGCTCTCTGAGGATGGCGAGCGGCTGCCCCCATCGTTGGCCAG
AA194047◂   CGTGGGGTGCTGCGGGGAGCTCTCTGAGGATGGCGAGCGGCTGCCCCCATCGTTGGCCAG 2480              2500              2520
            CGGGAGCTGCAGGGTGGGCCTGGGCCGCTGGGGGCTGATATCCAGGTTGAGGTCGATCCT
H85962▸
MKK7.cds◂   CGGGAGCTGCAGGGTGGGCCTGGGCCGCTGGGGGCTGATATCCAGGTTGAGGTCGATCCT
AA194047◂   CGGGAGCTGCAGGGTGGGCCTGGGCCGCTGGGGGCTGATATCCAGGTTGAGGTCGATCCT
```

*Fig. 1F*

```
                          2540           2560           2580
            CCGCCGGGCCTCCCGGTTCTCCTGCTTCAGCTTTGCTTCCAGGCGGGACAGCTTCTGTTC
H85962    ▶
MKK7.cds  ◀ CCGCCGGGCCTCCCGGTTCTCCTGCTTCAGCTTTGCTTCCAGGCGGGACAGCTTCTGTTC
AA194047  ◀ CCGCCGGGCCTCCCGGTTCTCCTGCTTCAGCTTTGCTTCCAGGCGGGACAGCTTCTGTTC 2600           2620           2640
            CAGGGAGGACGCCGCCATCTTCCCCGCCGCCACCGCCGCCGCGCACCGCCCGGCCGCCCG
H85962    ▶
MKK7.cds  ◀ CAGGGAGGACGCCGCCAT
AA194047  ◀ CAGGGAGGACGCCGCCATCTTCCCCGCCGCCACCGCCGCCGCGCACCGCCCGGCCGCCCG 2660           2680           2700
            TCAGTCCGGCAGACAAACACCTCGTGCCGAATTCTTGGCCTCGAGGGCCAAATTCCCTAT
H85962    ▶
MKK7.cds  ◀
AA194047  ◀ TCAGTCCGGCAGACAAACACCTCGTGCCGAATTCTTGGCCTCGAGGGCCAAATTCCCTAT 2720           2740           2760
            AGT
H85962    ▶
MKK7.cds  ◀
AA194047  ◀ AGT
```

*Fig. 1G*

```
mMKK7a   1 MAASSLEQKLSRLEAKLKQENREARRRIDLNLDISPQRPRPTLQLPLANDGGSRSPSSES  60
hMKK7    1 MAASSLEQKLSRLEAKLKQENREARRRIDLNLDISPQRPRPTLQLPLANDGGSRSPSSES  60
           ************************************************************ mMKK7a  61 SPQHPTPPTRPRHMLGLPSTLFTPRSMESIEIDQKLQEIMKQTGYLTIGGQRYQAEINDL 120
hMKK7   61 SPQHPTPPARPRHMLGLPSTLFTPRSMESIEIDQKLQEIMKQTGYLTIGGQRYQAEINDL 120
           ****** ************************************************* mMKK7a 121 ENLGEMGSGTCGQVWKMRFRKTGHIIAVKQMRRSGNKEENKRILMDLDVVLKSHDCPYIV 180
hMKK7  121 ENLGEMGSGTCGQVWKMRFRKTGHVIAVKQMRRSGNKEENKRILMDLDVVLKSHDCPYIV 180
           ********************** ********************************* mMKK7a 181 QCFGTFITNTDVFIAMELMGTCAEKLKKRMQGPIPERILGKMTVAIVKALYYLKEKHGVI 240
hMKK7  181 QCFGTFITNTDVFIAMELMGTCAEKLKKRMQGPIPERILGKMTVAIVKALYYLKEKHGVI 240
           ************************************************************ mMKK7a 241 HRDVKPSNILLDERGQIKLCDFGISGRLVDSKAKTRSAGCAAYMAPERIDPPDPTKPDYD 300
hMKK7  241 HRDVKPSNILLDERGQIKLCDFGISGRLVDSKAKTRSAGCAAYMAPERIDPPDPTKPDYD 300
           ************************************************************ mMKK7a 301 IRADVWSLGISLVELATGQFPYKNCKTDFEVLTKVLQEEPPLLPGHMGFSGDFQSFVKDC 360
hMKK7  301 IRADVWSLGISLVELATGQFPYKNCKTDFEVLTKVLQEEPPLLPGHMGFSGDFQSFVKDC 360
           ************************************************************ mMKK7a 361 LTKDHRKRPKYNKLLEHSFIKHYEILEVDVASWFKDVMAKTESPRTSGVLSQHHLPFFR- 419
hMKK7  361 LTKDHRKRPKYNKLLEHSFIKRYETLEVDVASWFKDVMAKTESPRTSGVLSQPHLPFFR- 419
           ********************* ** *************************** ******
```

*Fig. 2*

```
dMKK7    1 MSTIEFETIGSRLQSLEAKLQAQN-ESHDQIVLSGARGPVVSGSVPSARVPPLATSASAA  59
mMKK7a   1       MAASSLEQKLSRLEAKLKQENREARRRIDLN------------------LDIS----  35
hMKK7    1       MAASSLEQKLSRLEAKLKQENREARRRIDLN------------------LDIS----  35
                  .  .. . ***** . * . . * *                              * * dMKK7   60 TSATHAPSLGASSVSGSGISIAQRPAPPVPHATLRSPSASSSSSSRSAFRSAAPATGLRW 119
mMKK7a  36 ------P--------------QRPRP-----TLQLPLANDGGS-RSPSSESSPQ----- 63
hMKK7   36 ------P--------------QRPRP-----TLQLPLANDGGS-RSPSSESSPQ----- 63
                 *                  *** *      ** . * *   * **    ..* dMKK7  120 TYTPPTTRVSRATPTLPMLSSGPGGDVECTRPVILPLPTPPHPPVSETDMKLKIIMEQTG 179
mMKK7a  64 ---HPTP------PTRPRHMLG----------LPSTLFTPRSMESIEIDQKLQEIMKQTG 104
hMKK7   64 ---HPTP------PARPRHMLG----------LPSTLFTPRSMESIEIDQKLQEIMKQTG 104
              **       * . *  *          . * **      * *  . *** dMKK7  180 KLNINGRQYPTDINDLKHLGDLGNGTSGNVVKMMHLSSNTIIAVKQMRRTGNAEENKRIL 239
mMKK7a 105 YLTIGGQRYQAEINDLENLGEMGSGTCGQVWKMRFRKTGHIIAVKQMRRSGNKEENKRIL 164
hMKK7  105 YLTIGGQRYQAEINDLENLGEMGSGTCGQVWKMRFRKTGHVIAVKQMRRSGNKEENKRIL 164
            * * . *  **   . * ** * *            ***  ******* dMKK7  240 MDLDVVLKSHDCKYIVKCLGCFVRDPDVWICMELMSMCFDKLLKLSKKPVPEQILGKVTV 299
mMKK7a 165 MDLDVVLKSHDCPYIVQCFGTFITNTDVFIAMELMGTCAEKLKKRMQGPIPERILGKMTV 224
hMKK7  165 MDLDVVLKSHDCPYIVQCFGTFITNTDVFIAMELMGTCAEKLKKRMQGPIPERILGKMTV 224
           ********** * . *   *  ** * **** *  * ** *    * dMKK7  300 ATVNALSYLKDKHGVIHRDVKPSNILIDERGNIKLCDFGISGRLVDSKANTRSAGCAAYM 359
mMKK7a 225 AIVKALYYLKEKHGVIHRDVKPSNILLDERGQIKLCDFGISGRLVDSKAKTRSAGCAAYM 284
hMKK7  225 AIVKALYYLKEKHGVIHRDVKPSNILLDERGQIKLCDFGISGRLVDSKAKTRSAGCAAYM 284
           * *  * .*************.  .*************  ******** dMKK7  360 APERIDP---KKPKYDIRADVWSLGITLVELATARSPYEGCNTDFEVLTKVLDSEPPCLP 416
mMKK7a 285 APERIDPPDPTKPDYDIRADVWSLGISLVELATGQFPYKNCKTDFEVLTKVLQEEPPLLP 344
hMKK7  285 APERIDPPDPTKPDYDIRADVWSLGISLVELATGQFPYKNCKTDFEVLTKVLQEEPPLLP 344
           *****     *********** **    * ******* * ** dMKK7  417 YGEGYNFSQQFRDFVIKCLTKNHQDRPKYPELLAQPFIRIYESAKVDVPNWFQSIKDND- 475
mMKK7a 345 GHMG--FSGDFQSFVKDCLTKDHRKRPKYNKLLEHSFIKHYEILEVDVASWFKDVMAKTE 402
hMKK7  345 GHMG--FSGDFQSFVKDCLTKDHRKRPKYNKLLEHSFIKRYETLEVDVASWFKDVMAKTE 402
             * **  * ** **** **** . **** *** *** ** **  *** **  .

dMKK7  476 ----CGQWRSNAPEVT - 487
mMKK7a 403 SPRTSGVLSQHHLPFFR- 419
hMKK7  403 SPRTSGVLSQHHLPFFR- 419
                    *
```

Fig. 3

```
mMKK7a.cds    1 ATGGCGGCGTCCTCCCTGGAGCAGAAGCTGTCCCGCCTGGAAGCCAAGCTGAAGCAGGAG   60
hMKK7.cds     1 ATGGCGGCGTCCTCCCTGGAACAGAAGCTGTCCCGCCTGGAAGCAAAGCTGAAGCAGGAG   60
                ****************** **************** ************ mMKK7a.cds   61 AACCGTGAGGCCCGCAGGAGGATCGACCTCAACTTGGATATCAGCCCACAGCGGCCCAGG  120
hMKK7.cds    61 AACCGGGAGGCCCGGACGAGGATCGACCTCAACCTGGATATCAGCCCCCAGCGGCCCAGG  120
                *** **** ************  ********* ********* mMKK7a.cds  121 CCCACCCTGCAACTCCCACTGGCCAACGATGGGGGCAGCCGCTCACCATCCTCAGAGAGC  180
hMKK7.cds   121 CCCACCCTGCAGCTCCCGCTGGCCAACGATGGGGGCAGCCGCTCGCCATCCTCAGAGAGC  180
                ********* * ********************** ************ mMKK7a.cds  181 TCCCCACAGCACCCTACACCCCCCACCCGGCCCCGCCACATGCTGGGGCTCCCATCAACC  240
hMKK7.cds   181 TCCCCGCAGCACCCCACGCCCCCCGCCCGGCCCCGCCACATGCTGGGGCTCCCGTCAACC  240
                *** ****  **** ********************** **** mMKK7a.cds  241 TTGTTCACACCGCGCAGTATGGAGAGCATCGAGATTGACCAGAAGCTGCAGGAGATCATG  300
hMKK7.cds   241 CTGTTCACACCCCGCAGCATGGAGAGCATTGAGATTGACCAGAAGCTGCAGGAGATCATG  300
                 ******** * ******* **************************** mMKK7a.cds  301 AAGCAGACAGGGTACCTGACTATCGGGGGCCAGCGTTATCAGGCAGAAATCAATGACTTG  360
hMKK7.cds   301 AAGCAGACGGGCTACCTGACCATCGGGGGCCAGCGCTACCAGGCAGAAATCAACGACCTG  360
                ******  ****** **********   ********** * ** mMKK7a.cds  361 GAGAACTTGGGTGAGATGGGCAGTGGTACCTGTGGTCAGGTGTGGAAGATGCGGTTCCGG  420
hMKK7.cds   361 GAGAACTTGGGCGAGATGGGCAGCGGCACCTGCGGCCAGGTGTGGAAGATGCGCTTCCGG  420
                ********* *******  ***  *************** **** mMKK7a.cds  421 AAGACAGGCCACATCATTGCTGTTAAGCAAATGCGGCGCTCTGGGAACAAGGAAGAGAAT  480
hMKK7.cds   421 AAGACCGGCCACGTCATTGCCGTTAAGCAAATGCGGCGCTCCGGGAACAAGGAGGAGAAC  480
                *** ** *** **************** ******* *** mMKK7a.cds  481 AAGCGCATTTTGATGGACCTGGATGTAGTACTCAAGAGCCATGACTGCCCTTACATCGTT  540
hMKK7.cds   481 AAGCGCATCCTCATGGACCTGGATGTGGTGCTGAAGAGCCACGACTGCCCCCTACATCGTG  540
                ********  * ************   **** **** ****** mMKK7a.cds  541 CAGTGCTTTGGCACCTTCATCACCAACACAGACGTCTTTATTGCCATGGAGCTCATGGGC  600
hMKK7 cds   541 CAGTGCTTTGGGACGTTCATCACCAACACGGACGTCTTCATCGCCATGGAGCTCATGGGC  600
                *********  ************ ****  *  *************** mMKK7a.cds  601 ACATGTGCAGAGAAGCTGAAGAAACGAATGCAGGGCCCCATTCCAGAGCGAATCCTGGGC  660
hMKK7.cds   601 ACCTGCGCTGAGAAGCTCAAGAAGCGGATGCAGGGCCCCATCCCCGAGCGCATTCTGGGC  660
                ** ** ** ******** ***** ** ************* ** ***** ** ******
```

*Fig. 4A*

```
mMKK7a.cds  661 AAGATGACTGTGGCGATTGTGAAAGCACTGTACTATCTGAAGGAGAAGCATGGCGTCATC  720
hMKK7.cds   661 AAGATGACAGTGGCGATTGTGAAGGCGCTGTACTACCTGAAGGAGAAGCACGGTGTCATC  720
                ***** **********  ***** **********  ***** mMKK7a.cds  721 CATCGCGATGTCAAACCCTCCAACATCCTGCTAGATGAGCGGGGCCAGATCAAGCTCTGT  780
hMKK7.cds   721 CACCGCGACGTCAAGCCCTCCAACATCCTGCTGGACGAGCGGGGCCAGATCAAGCTCTGC  780
                 * * ************  ********************* mMKK7a.cds  781 GACTTTGGCATCAGTGGCCGTCTTGTTGACTCCAAAGCCAAAACACGGAGTGCTGGCTGT  840
hMKK7.cds   781 GACTTCGGCATCAGCGGCCGCCTGGTGGACTCCAAAGCCAAGACGCGGGAGCGCCGGCTGT  840
                *** **** *   **********  ***  ****** mMKK7a.cds  841 GCTGCCTATATGGCTCCCGAGCGCATCGACCCTCCAGATCCCACCAAGCCTGACTATGAC  900
hMKK7.cds   841 GCCGCCTACATGGCACCCGAGCGCATTGACCCCCAGACCCCACCAAGCCGGACTATGAC  900
                 * * ****** * * ****** ******* mMKK7a.cds  901 ATCCGAGCTGATGTGTGGAGCCTGGGCATCTCACTGGTGGAGCTGGCAACAGGACAGTTC  960
hMKK7.cds   901 ATCCGGGCCGACGTATGGAGCCTGGGCATCTCGTTGGTGGAGCTGGCAACAGGACAGTTT  960
                ***    *************   ********************** mMKK7a.cds  961 CCCTATAAGAACTGCAAGACGGACTTTGAGGTCCTCACCAAAGTCCTACAGGAAGAGCCC 1020
hMKK7.cds   961 CCCTACAAGAACTGCAAGACGGACTTTGAGGTCCTCACCAAAGTCCTACAGGAAGAGCCC 1020
                *** **************************************************** mMKK7a.cds 1021 CCACTCCTGCCTGGTCACATGGGCTTCTCAGGGGACTTCCAGTCATTTGTCAAAGACTGC 1080
hMKK7.cds  1021 CCGCTTCTGCCCGGACACATGGGCTTCTCGGGGGACTTCCAGTCCTTCGTCAAAGACTGC 1080
                  ***  ************ **********  *********** mMKK7a.cds 1081 CTTACTAAAGATCACAGGAAGAGACCAAAGTATAATAAGCTACTTGAACACAGTTTCATC 1140
hMKK7.cds  1081 CTTACTAAAGATCACAGGAAGAGACCAAAGTATAATAAGCTACTTGAACACAGCTTCATC 1140
                *************************************************** **** mMKK7a.cds 1141 AAGCACTATGAGATACTCGAGGTGGATGTCGCGTCCTGGTTTAAGGATGTCATGGCGAAG 1200
hMKK7.cds  1141 AAGCGCTACGAGACGCTGGAGGTGGACGTGGCGTCCTGGTTCAAGGATGTCATGGCGAAG 1200
                ** * **   *****  ******* ***************** mMKK7a.cds 1201 ACCGAGTCCCCAAGGACTAGTGGAGTCCTGAGTCAGCACCATCTGCCCTTCTTCAGGTAG 1260
hMKK7.cds  1201 ACTGAGTCACCGCGGACTAGCGGCGTCCTGAGCCAGCCCCACCTGCCCTTCTTCAGGTAG 1260
                ** ***** **  ******* ** ******** ****    ** *****************
```

*Fig. 4B*

MITOGEN-ACTIVATED PROTEIN KINASE KINASE 7 (MKK7)

This application claims the benefit of co-pending provisional application Serial No. 60/070,114 filed Dec. 31, 1997, which is incorporated herein by reference.

TECHNICAL AREA OF THE INVENTION

The invention relates to the area of transduction of extracellular signals into the nucleus of human cells. More particularly, the invention relates to transduction of extracellular signals by means of mitogen-activated protein kinase kinase pathways.

BACKGROUND OF THE INVENTION

The mitogen-activated protein kinase (MAPK) cascade is a major signaling system by which cells transduce extracellular cues into intracellular responses. MAPKs phosphorylate substrates on serine or threonine residues adjacent to proline residues and are thus proline-directed protein kinases, as described in Cano and Mahadevan, *TIBS Reviews* 20:117–122 (1995). It is believed that multiple MAPK cascades exist, thus implicating many other molecules in the up- and downstream events contributing to MAPK signal transduction events.

The c-Jun $NH_2$-terminal kinase (JNK), or stress-activated protein kinase (SAPK), signal transduction pathway is activated in response to cellular stresses, including DNA damage, heat shock, and UV light, as well as by proinflammatory cytokines, such as TNFα. (Gupta et al., 1996, *EMBO J.* 15:2760–70; Derijard et al., 1994, *Cell* 76:1025–37; Kyriakis et al., 1994, *Nature* 369:156–60; and Kallunki et al., 1994, *Genes Dev.* 8:2996–3007). After activation, JNK binds to and phosphorylates transcription factors such as ATF2 and c-Jun, which increases transcription of genes activated by these factors. Whitmarsh et al., 1996, *J. Mol. Med.* 74:589–607.

The pathways responsible for transducing environmental stress signals through JNK have not been fully described. Thus, there is a need in the art for the identification of proteins which are involved in JNK stress signal transduction pathways. Such proteins can be manipulated, for example, to protect cells against stress due to disease or environmental conditions.

SUMMARY OF THE INVENTION

It is an object of the invention to provide the amino acid sequence and DNA coding sequence of a unique member of the MAP kinase kinase family. This and other objects of the invention are provided by one or more of the embodiments described below.

One embodiment of the invention is an isolated and purified human mitogen-activated protein kinase kinase 7 (MKK7) protein having an amino acid sequence which is at least 99% identical to SEQ ID NO:2. Percent identity is determined using a Smith-Waterman homology search algorithm using an affine gap search with a gap open penalty of 12 and a gap extension penalty of 1.

Still another embodiment of the invention is an MKK7 fusion protein comprising a first protein segment and a second protein segment fused together by means of a peptide bond. The first protein segment consists of a human MKK7 protein as shown in SEQ ID NO:2.

Even another embodiment of the invention is a cDNA molecule which encodes a human MKK7 protein having an amino acid sequence which is at least 99% identical to SEQ ID NO:2. Percent identity is determined using a Smith-Waterman homology search algorithm using an affine gap search with a gap open penalty of 12 and a gap extension penalty of 1.

Another embodiment of the invention is a cDNA molecule which is at least 85% identical to the nucleotide sequence shown in SEQ ID NO:1. Percent identity is determined using a Smith-Waterman homology search algorithm as implemented in a MPSRCH program using an affine gap search with a gap open penalty of 12 and a gap extension penalty of 1.

A further embodiment of the invention is an isolated and purified subgenomic polynucleotide comprising a nucleotide sequence which hybridizes to SEQ ID NO:1 after washing with 0.2×SSC at 65° C. The nucleotide sequence encodes a human MKK7 protein having the amino acid sequence of SEQ ID NO:2.

Still another embodiment of the invention is a construct comprising a promoter and a polynucleotide segment encoding a human MKK7 protein as shown in SEQ ID NO:2. The polynucleotide segment is located downstream from the promoter. Transcription of the polynucleotide segment initiates at the promoter.

Yet another embodiment of the invention is a host cell comprising a construct which comprises a promoter and a polynucleotide segment encoding a human MKK7 protein as shown in SEQ ID NO:2.

A further embodiment of the invention is a recombinant host cell comprising a new transcription initiation unit. The new transcription initiation unit comprises in 5' to 3' order an exogenous regulatory sequence, an exogenous exon, and a splice donor site. The new transcription initiation unit is located upstream of a coding sequence of an MKK7 gene as shown in SEQ ID NO:1. The exogenous regulatory sequence controls transcription of the coding sequence of the MKK7 gene.

Even another embodiment of the invention is a polynucleotide probe comprising at least 12 contiguous nucleotides of SEQ ID NO:1 and a detectable label.

Another embodiment of the invention is a method of increasing transcription of a gene responsive to an AP-1 transcription factor. A cell is contacted with a polynucleotide encoding all or a portion of an MKK7 protein under conditions where said all or a portion of the MKK7 protein phosphorylates a c-Jun $NH_2$ terminal kinase. Phosphorylation of the c-Jun $NH_2$-terminal kinase thereby phosphorylates an AP-1 transcription factor. Transcription of the gene is thereby increased.

Still another embodiment of the invention is a method of decreasing transcription of a gene responsive to an AP-1 transcription factor. A cell is contacted with a polynucleotide encoding a reagent which binds to an MKK7 gene or expression product. The ability of MKK7 protein to phosphorylate a c-Jun $NH_2$-terminal kinase is thereby decreased.

Yet another embodiment of the invention is a method of inducing apoptosis of a cell. A cell is contacted with a polynucleotide encoding all or a portion of an MKK7 expression product. The all or a portion of the MKK7 expression product is capable of inducing apoptosis of the cell. Apoptosis of the cell is thereby induced.

Even another embodiment of the invention is a method of preventing apoptosis of a cell. A cell is contacted with a reagent which binds to an MKK7 gene or expression product. Apoptosis of the cell is thereby prevented.

A further embodiment of the invention is a method of identifying a test compound which modulates signal transduction through a JNK pathway. A biological sample is contacted with a test compound. Phosphorylation or synthesis of an MKK7 protein ash shown in SEQ ID NO:2 or phosphorylation of a substrate of the MKK7 protein is detected. A test compound which increases or decreases phosphorylation or synthesis of the MKK7 protein or phosphorylation of the MKK7 substrate identifies a potential drug for modulating signal transduction through the JNK pathway.

The present invention provides the art with the amino acid sequence and DNA coding sequence of human MKK7, a unique member of the MAP kinase kinase family. The invention can be used, inter alia, to regulate gene transcription and to effect or prevent apoptosis.

BRIEF DESCRIPTION OF THE DRAWINGS

FIG. 1 illustrates the alignment of the MKK7 (SEQ ID NOS: 1 and 8) coding sequence with EST sequences AA194047 (SEQ ID NO:3) and h85962 (SEQ ID NO:4) and a consensus sequence (SEQ ID NO:9).

FIG. 2 compares mouse (SEQ ID NO:5) and human MKK7 (SEQ ID NO:2) amino acid sequences.

FIG. 3 compares mouse (SEQ ID NO:5), human (SEQ ID NO:2), and Drosophila (SEQ ID NO:6) MKK7 amino acid sequences.

FIG. 4 compares human (SEQ ID NO:1) and mouse (SEQ ID NO:7) MKK7 coding sequences.

DETAILED DESCRIPTION OF THE INVENTION

A unique member of the human MAP kinase kinase family has been discovered. Human MKK7 protein has the sequence disclosed in SEQ ID NO:2. Protein variants of MKK7 protein are also included in the invention. Protein variants can be naturally or non-naturally occurring. Naturally occurring MKK7 variants are those which are found in humans or other species and which comprise amino acid sequences which are substantially identical to the amino acid sequence shown in SEQ ID NO:2.

Preferably, naturally or non-naturally occurring protein variants of the invention have amino acid sequences which are at least 85%, 90%, or 95% identical to the amino acid sequence shown in SEQ ID NO:2 have similar biological properties (see below). More preferably, the molecules are 98% or 99% identical. Percent sequence identity between a putative human MKK7 variant and the amino acid sequence of SEQ ID NO:2 is determined using the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482–489.

Amino acids which are not involved in regions which determine biological activity can be deleted or modified without affecting biological function to form non-naturally occurring protein variants of the invention. Modifications of interest in the protein sequences can include the alteration, substitution, replacement, insertion or deletion of a selected amino acid residue. Proteins or derivatives can be either glycosylated or unglycosylated. Techniques for making such modifications are well known to those skilled in the art (see, e.g., U.S. Pat. No. 4,518,584). Alternatively, variants of MKK7 protein can be constructed using techniques of synthetic chemistry or using recombinant DNA methods.

A subset of mutants, called muteins, is a group of polypeptides with the non-disulfide bond participating cysteines substituted with a neutral amino acid, generally, with serines. These mutants may be stable over a broader temperature range than MKK7. See Mark et al., U.S. Pat. No. 4,959,314.

Guidance in determining which amino acid residues may be substituted, inserted, or deleted without abolishing biological or immunological activity may be found using computer programs well known in the art, such as DNASTAR software. Preferably, amino acid changes in variants or derivatives of proteins of the invention are conservative amino acid changes, i.e., substitutions of similarly charged or uncharged amino acids. A conservative amino acid change involves substitution of one amino acid for another amino acid of a family of amino acids which are structurally related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule, especially if the replacement does not involve an amino acid at a binding site involved in an interaction of the protein. Non-naturally occurring amino acids can also be used to form protein variants of the invention.

Whether an amino acid change results in a functional MKK7 protein or polypeptide can readily be determined by assaying its ability to phosphorylate a substrate such as c-Jun $NH_2$-terminal kinase. In vitro kinase assays are taught, for example, in WO 96/36642.

Alternatively, variants with one or more altered biological activities. For example, an arginine can be substituted for the lysine at position 149 of SEQ ID NO:2 in order to alter the ATP binding site of MKK7 and generate a "kinase dead" mutant form of the protein.

MKK7 protein is useful, inter alia, for generating antibodies against MKK7 protein sequences. Polypeptide fragments polypeptides of a human MKK7 protein, comprising at least 6, 8, 10, 12, 15, 18, 20, 22, 23, 24, 25, 30, 35, 40, 45, 50, 55, 60, 65, 70, 75, 100, 125, 150, 175, 200, 250, 300, 350, or 400 consecutive amino acids selected from SEQ ID NO:2 can be used, for example, as immunogens.

MKK7 protein can be isolated and purified from human cells which express MKK7 protein, such as heart, brain, lung, liver, muscle, kidney, and testis. MKK7 can be obtained substantially free from other human proteins by standard protein purification methods, such as size exclusion chromatography, ion exchange chromatography, ammonium sulfate fractionation, affinity chromatography, or preparative gel electrophoresis. Enzymes can be used to generate MKK7 polypeptides by enzymatic proteolysis of full-length MKK7 protein.

Human MKK7 proteins, polypeptides, or variants can be produced by recombinant DNA methods or by synthetic chemical methods. For production of recombinant MKK7 proteins or polypeptides, MKK7 coding sequences selected from the nucleotide sequence shown in SEQ ID NO:1 can be expressed in known prokaryotic or eukaryotic expression systems. Bacterial, yeast, insect, or mammalian expression systems can be used, as is known in the art.

Alternatively, synthetic chemical methods, such as solid phase peptide synthesis, can be used to synthesize human MKK7 protein, polypeptides, or variants. General means for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, B. Weinstein (1983). Substitution of D-amino acids for the normal L-stereoisomer of MKK7 can be carried out to increase the half-life of the molecule.

MKK7 protein or polypeptides can also be used in a fusion protein, for example as an immunogen. A fusion protein can be used, for example, to target MKK7 protein or MKK7 polypeptides to a particular location in a cell or tissue, and to use K7 protein or polypeptides in various assays, such as the yeast two-hybrid technique.

The fusion protein comprises two protein segments. The first protein segment consists of at least 6, 8, 10, 12, 15, 18, 20, 22, 23, 24, 25, 30, 35, 40, 45, 50, 55, 60, 65, 70, 75, 100, 125, 150, 175, 200, 250, 300, 350, or 400 contiguous amino acids of MKK7 selected from the amino acid sequence shown in SEQ ID NO:2. The first protein segment can also consist of the amino acid sequence shown in SEQ ID NO:2.

The first protein segment is fused to a second protein segment by means of a peptide bond. The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (GFP), glutathione-S-transferase (GST), luciferase, horseradish peroxidase (HRP), and chloramphenicol acetyltransferase (CAT). Epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions.

MKK7 fusion proteins can be made by covalently linking the first and second protein segments or by standard procedures in the art of molecular biology. Recombinant DNA methods can be used to prepare MKK7 fusion proteins, for example, by making a DNA construct which comprises coding sequences selected from SEQ ID NO:1 in proper reading frame with nucleotides encoding the second protein segment and expressing the DNA construct in a host cell, as is known in the art. Many kits for constructing fusion proteins are available from companies which supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Isolated and purified MKK7 proteins, polypeptides, biologically active or altered variants, or fusion proteins can be used as immunogens, to obtain preparations of antibodies which specifically bind to epitopes of an MKK7 protein or biologically active or altered variant. Preferably, MKK7 epitopes are not present in other human proteins. Typically, at least 6, 8, 10, or 12 contiguous amino acids are required to form an MKK7 epitope. However, epitopes which involve non-contiguous amino acids may require more, e.g., at least 15, 25, or 50 amino acids.

Antibodies which specifically bind to epitopes of MKK7 proteins, polypeptides, fusion proteins, or biologically active variants can be used in immunochemical assays, including but not limited to Western blots, ELISAs, radioimmunoassays, immunohistochemical assays, immunoprecipitations, or other immunochemical assays known in the art. Typically, MKK7-specific antibodies provide a detection signal at least 5-, 10-, or 20-fold higher than a detection signal provided with other proteins when used in such immunochemical assays. Preferably, antibodies which specifically bind to MKK7 epitopes do not detect other proteins in immunochemical assays and can immunoprecipitate MKK7 protein or polypeptides from solution.

Epitopes of MKK7 which are particularly antigenic can be selected, for example, by routine screening of MKK7 polypeptides for antigenicity or by applying a theoretical method for selecting antigenic regions of a protein to the amino acid sequence shown in SEQ ID NO:2. Such methods are taught, for example, in Hopp and Wood, *Proc. Natl. Acad. Sci. U.S.A.* 78, 3824–28 (1981), Hopp and Wood, *Mol. Immunol.* 20, 483–89 (1983), and Sutcliffe et al., *Science* 219, 660–66 (1983). By reference to FIGS. 2 and 3, regions of the human MKK7 protein which would be cross-reactive with the proteins of other species can be avoided, if desired.

Any type of antibody known in the art can be generated to bind specifically to MKK7 epitopes. For example, preparations of polyclonal and monoclonal antibodies can be made using standard methods which are well known in the art. Similarly, single-chain antibodies can also be prepared. Single-chain antibodies which specifically bind to MKK7 epitopes can be isolated, for example, from single-chain immunoglobulin display libraries, as is known in the art. The library is "panned" against MKK7 amino acid sequences, and a number of single chain antibodies which bind with high-affinity to different epitopes of MKK7 protein can be isolated. Hayashi et al., 1995, *Gene* 160:129–30. Single-chain antibodies can also be constructed using a DNA amplification method, such as the polymerase chain reaction (PCR), using hybridoma cDNA as a template. Thirion et al., 1996, *Eur. J. Cancer Prev.* 5:507–11.

Single-chain antibodies can be mono- or bispecific, and can be bivalent or tetravalent. Construction of tetravalent, bispecific single-chain antibodies is taught, for example, in Coloma and Morrison, 1997, *Natl. Biotechnol.* 15:159–63. Construction of bivalent, bispecific single-chain antibodies is taught inter alia in Mallender and Voss, 1994, *J. Biol. Chem.* 269:199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497–501; Nicholls et al., 1993, *J. Immunol. Meth.* 165:81–91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementarity determining regions. Alternatively, one can produce humanized antibodies using recombinant methods, as described in GB2188638B. Antibodies which specifically bind to MKK7 epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 93/03151. Binding proteins which are derived from immunoglobulins and which are multivalent and multispecific, such as the "diabodies" described in WO 94/13804, can also be prepared.

MKK7-speciifc antibodies can be purified by methods well known in the art. For example, antibodies can be affinity purified by passing the antibodies over a column to which an MKK7 protein, polypeptide, biologically active variant, or fusion protein is bound. The bound antibodies can then be eluted from the column, using a buffer with a high salt concentration.

MKK7-specific binding polypeptides other than antibodies can also be generated. MKK7-specific binding polypeptides are polypeptides which bind with MKK7 or its variants and which have a measurably higher binding affinity for MKK7 and polypeptide derivatives of MKK7 than for other polypeptides tested for binding. Higher affinity by a factor of 10 is preferred, more preferably a factor of 100. Such polypeptides can be found, for example, using the yeast two-hybrid system.

Antibodies can be used, inter alia, to detect wild-type MKK7 protein in human tissue and fractions thereof. The antibodies can also be used to detect the presence of mutations in the MKK7 gene which result in under- or overexpression of an MKK7 protein or in expression of an MKK7 protein with altered size or electrophoretic mobility. Optionally, antibodies can be used to block MKK7 cyclin binding sites or to alter effective levels of functional MKK7 protein.

The invention also provides subgenomic polynucleotides which encodes MKK7 proteins, polypeptides, biologically active or altered variants, fusion proteins, and the like. MKK7 subgenomic polynucleotides contain less than a whole chromosome and can be double- or single-stranded. Preferably, the polynucleotides are intron-free.

Purified and isolated MKK7 subgenomic polynucleotides can comprise at least 11, 20, 25, 30, 35, 40, 45, 50, 55, 60, 67, 70, 75, 100, 125, 150, 200, 250, or 300, or more contiguous nucleotides selected from the nucleotide sequence shown in SEQ ID NO:1 or its complement. SEQ ID NO:1 is the coding sequence of the human MKK7 gene.

The complement of the nucleotide sequence shown in SEQ ID NO:1 can be used provide MKK7 antisense oligonucleotides. MKK7 subgenomic polynucleotides also include polynucleotides which encode MKK7-specific single-chain antibodies, ribozymes, and biologically active or altered MKK7 variants.

Degenerate nucleotide sequences encoding amino acid sequences of MKK7 protein or biologically active MKK7 variants, as well as homologous nucleotide sequences which are at least 65%, 75%, 85%, 90%, 95%, 96%, 97%, 98%, or 99% identical to the nucleotide sequence shown in SEQ ID NO:1, are also MKK7 subgenomic polynucleotides. Percent sequence identity between the nucleotide sequence of SEQ ID NO:1 and a putative homologous or degenerate MKK7 nucleotide sequence is determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to the coding sequence shown in SEQ ID NO:1 or its complement with at most 1, 2, 3, 4, 5, 10, 15, 20, 25, 30, or 35% basepair mismatches are also MKK7 subgenomic polynucleotides of the invention. For example, using the following wash conditions—2×SSC (0.3 M sodium chloride, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous MKK7 sequences can be identified which contain at most about 25–30% basepair mismatches with SEQ ID NO:1 or its complement. More preferably, homologous nucleic acid strands contain 15–25% basepair mismatches, even more preferably 5–15% basepair mismatches.

Species homologs of MKK7 subgenomic polynucleotides of the invention can also be identified by making suitable probes or primers and screening cDNA expression libraries from other species, such as mice, monkeys, yeast, or bacteria. It is well known that the $T_m$ of a double-stranded DNA decreases by 1–1.5° C. with every 1% decrease in homology (Bonner et al., *J. Mol. Biol.* 81, 123 (1973). Homologous MKK7 human polynucleotides or MKK7 polynucleotides of other species can therefore be identified, for example, by hybridizing a putative homologous MKK7 polynucleotide with a polynucleotide having the nucleotide sequence of SEQ ID NO:1, comparing the melting temperature of the test hybrid with the melting temperature of a hybrid comprising a polynucleotide having SEQ ID NO:1 and a polynucleotide which is perfectly complementary to SEQ ID NO:1, and calculating the number of basepair mismatches within the test hybrid.

Nucleotide sequences which hybridize to the coding sequence shown in SEQ ID NO:1 or its complement following stringent hybridization and/or wash conditions are also MKK7 subgenomic polynucleotides of the invention. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions, a combination of temperature and salt concentration should be chosen that is approximately 12–20° C. below the calculated $T_m$ of the hybrid under study. The $T_m$ of a hybrid between the MKK7 sequence shown in SEQ ID NO:1 and a polynucleotide sequence which is 65%, 75%, 85%, 90%, 95%, 96%, 97%, 98%, or 99% identical to SEQ ID NO:1 can be calculated, for example, using the equation of Bolton and McCarthy, *Proc. Natl. Acad. Sci. U.S.A.* 48, 1390 (1962):

$$T_m=81.5° C.-16.6(\log_{10}[Na^+])+0.41(\%G+C)-0.63(\%formamide)-600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

MKK7 subgenomic polynucleotides can be isolated and purified free from other nucleotide sequences using standard nucleic acid purification techniques. For example, restriction enzymes and probes can be used to isolate polynucleotide fragments which comprise nucleotide sequences encoding an MKK7 protein or variant. Isolated and purified subgenomic polynucleotides are in preparations which are free or at least 90% free of other molecules.

Complementary DNA (cDNA) molecules which encode MKK7 proteins are also MKK7 subgenomic polynucleotides of the invention. MKK7 cDNA molecules can be made with standard molecular biology techniques, using MKK7 mRNA as a template. MKK7 cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize MKK7 subgenomic polynucleotide molecules of the invention. The degeneracy of the genetic code allows alternate nucleotide sequences to be synthesized which will encode an MKK7 protein having the amino acid sequence shown in SEQ ID NO:2 or a biologically active variant of that sequence. All such nucleotide sequences are within the scope of the present invention.

The invention also provides polynucleotide probes which can be used to detect MKK7 sequences, for example, in hybridization protocols such as Northern or Southern blotting or in situ hybridization. Polynucleotide probes of the invention comprise at least 12, 13, 14, 15, 16, 17, 18, 19, 20, 30, or 40 or more contiguous nucleotides selected from SEQ ID NO:1. Polynucleotide probes of the invention can comprise a detectable label, such as a radioisotopic, fluorescent, enzymatic, or chemiluminescent label.

Purified and isolated MKK7 subgenomic polynucleotides can be used as primers to obtain additional copies of the polynucleotides or as probes for identifying wild-type and mutant MKK7 coding sequences. MKK7 subgenomic polynucleotides can also be used to express MKK7mRNA, protein, polypeptides, fusion proteins and the like and to generate MKK7 antisense oligonucleotides and ribozymes.

An MKK7 subgenomic polynucleotide comprising MKK7 coding sequences can be used in a construct, such as a DNA or RNA construct. The construct can be a vector and can be used to transfer an MKK7 subgenomic polynucleotide into a cell, for example, for propagation of the subgenomic polynucleotide. MKK7 constructs can be linear or circular molecules. They can be on autonomously replicating molecules or on molecules without replication sequences. They can be regulated by their own or by other regulatory sequences, as are known in the art.

An MKK7 construct can be an expression construct which comprises a promoter which is functional in a selected host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes, for example, all or a portion of an MKK7 protein, variant, fusion protein, antibody, or ribozyme. The polynucleotide segment is located downstream from the promoter. . Transcription of the polynucleotide segment initiates at the promoter.

A recombinant host cell comprising an MKK[7] construct can be constructed and used to express all or a portion of an MKK7 protein. Recombinant host cells comprising MKK7 expression constructs can be prokaryotic or eukaryotic. A variety of host cells are available for use in bacterial, yeast, insect, and human expression systems and can be used to express or to propagate MKK7 expression constructs (see below).

Constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation,. "gene gun," and calcium phosphate-mediated transfection.

Expression systems in bacteria include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad. Sci. USA* (1983) 80: 21–25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202 :302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. No. 4,837,148, U.S. Pat No. 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Natl. Acad. Sci. USA* (1984) 81: 1470–1474, Kelly and Hynes, EMBO J. (1985) 4: 475479; EP 244,234, and WO 91/00357.

Expression of MKK7 subgenomic polynucleotides in insects can be accomplished as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad. Sci. USA* (1985) 82: 8404, Miyajima et al., *Gene* (1987) 58: 273; and Martin et al., *DNA* (1988) 7.99. Numerous baculoviral strains and variants and corresponding permissive insect host cells from hosts are described in Luckow et al., *Bio/Technology* (1988) 6: 47–55, Miller et al., in GENETIC ENGINEERING (Setlow, J. K. et al. eds.), Vol. 8 (Plenum Publishing, 1986), pp. 277–279, and Maeda et al., *Nature*, (1985) 315: 592–594.

Mammalian expression of MKK7 subgenomic polynucleotides can be accomplished as described in Dijkema et al., *EMBO J.* (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. Pat. No. RE 30,985.

Polynucleotides of the invention can also be used in gene delivery vehicles, for the purpose of delivering an MKK7 mRNA or oligonucleotide (either with the sequence of native MKK7 mRNA or its complement), full-length MKK7 protein, MKK7 fusion protein, MKK7 polypeptide, or MKK7-specific ribozyme or single-chain antibody, into a cell preferably a eukaryotic cell. According to the present invention, a gene delivery vehicle can be, for example, naked plasmid DNA, a viral expression vector comprising an MKK7 polynucleotide, or an MKK7 polynucleotide in conjunction with a liposome or a condensing agent.

In one embodiment of the invention, the gene delivery vehicle comprises a promoter and an MKK7 polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

An MKK7 gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the MKK7 gene delivery vehicle is a recombinant retroviral vector. Recombinant retroviruses and various uses thereof have been described in numerous references including, for example, Mann et al., *Cell* 33:153, 1983, Cane and Mulligan, *Proc. Natl. Acad. Sci. USA* 81:6349, 1984, Miller et al., *Human Gene Therapy* 1:5–14, 1990, U.S. Pat. Nos. 4,405,712, 4,861,719, and 4,980,289, and PCT Application Nos. WO 89/02,468, WO 89/05,349, and WO 90/02, 806. Numerous retroviral gene delivery vehicles can be utilized in the present invention, including for example those described in EP 0,415,731; WO 90/07936; WO 94/03622; WO 93/25698; WO 93/25234, U.S. Pat. No. 5,219,740; WO 9311230, WO 9310218, Vile and Hart, *Cancer Res.* 53:3860–3864; 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO91/02805).

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al.,*J. Vir.* 49:828, 1984; and Oliff et al.,*J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector. Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Graffi (Ru et al.,*J. Vir.* 67:4722, 1993; and Yantchev Neoplasma 26:397, 1979), Gross (ATCC No. VR-590), Kirsten (Albino et al., *J. Exp. Med.* 164:1710, 1986), Harvey sarcoma virus (Manly et al.,*J. Vir.* 62:3540, 1988; and Albino et al., *J. Exp. Med.* 164:1710, 1986) and Rauscher (ATCC No. VR-998), and Moloney MLV (ATCC No. VR-190). A particularly preferred non-mouse retrovirus is Rous sarcoma virus. Preferred Rous sarcoma viruses include Bratislava (Manly et al., *J. Vir.* 62:3540, 1988; and Albino et al.,*J. Exp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral MKK7 gene delivery vehicles given the disclosure provided herein and standard recombinant techniques (e.g., Sambrook et al., MOLECULAR CLONING: A LABORATORY MANUAL, 2d ed., Cold Spring Harbor Laboratory Press, 1989, and Kunkle, *Proc. Natl. Acad. Sci. U.S.A.* 82:488, 1985) known in the art. Portions of retroviral MKK7 expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus. These recombinant retroviral vectors can be used to generate transduction competent retroviral vector particles by introducing them into appropriate packaging cell lines (see Ser. No. 07/800, 921, filed Nov. 29, 1991). Recombinant retroviruses can be produced which direct the site-specific integration of the recombinant retroviral genome into specific regions of the host cell DNA. Such site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805. These recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, Biotechniques 6:616–627, 1988, and Rosenfeld et al., *Science* 252:431–434, 1991, WO 93/07283, WO 93/06223, and WO 93/07282).

An MKK7 gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral MKK7 gene delivery vehicles can also be constructed and used to deliver MKK7 amino acids or nucleotides. The use of adeno-associated viral gene delivery vehicles in vitro is described in Chatterjee et al., *Science* 258: 1485–1488 (1992), Walsh et al., *Proc. Nat'l. Acad. Sci.* 89: 7257–7261 (1992), Walsh et al., *J. Clin. Invest.* 94: 1440–1448 (1994), Flotte et al., *J. Biol. Chem.* 268: 3781–3790 (1993), Ponnazhagan et al.,*J. Exp. Med.* 179: 733–738 (1994), Miller et al., *Proc. Nat'l Acad. Sci.* 91: 10183–10187 (1994), Einerhand et al, *Gene Ther.* 2: 336–343 (1995), Luo et al., *Exp. Hematol.* 23: 1261–1267 (1995), and Zhou et al., *Gene Therapy* 3: 223–229 (1996). In vivo use of these vehicles is described in Flotte et al., *Proc. Nat'l Acad. Sci.* 90:

10613–10617 (1993), and Kaplitt et al, *Nature Genet.* 8:148–153 (1994).

In another embodiment of the invention, an MKK7 gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for MKK7 polynucleotides. Alpha viruses are described in WO 94/21792, WO 92/10578 and WO 95/07994. Several different alphavirus gene delivery vehicle systems can be constructed and used to deliver MKK7 polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent fragment transcription, and a Sindbis RNA polymerase recognition sequence. Optionally, the viral junction region can be modified so that polynucleotide transcription is reduced, increased, or maintained. As will be appreciated by those in the art, corresponding regions from other alphaviruses can be used in place of those described above.

The viral junction region of an alphavirus-derived gene delivery vehicle can comprise a first viral junction region which has been inactivated in order to prevent transcription of the polynucleotide and a second viral junction region which has been modified such that polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450.

Other viral gene delivery vehicles suitable for use in the present invention include, for example, those derived from poliovirus (Evans et al, *Nature* 339:385, 1989, and Sabin et al, *J. Biol. Standardization* 1:115, 1973) (ATCC VR-58); rhinovirus (Arnold et al., *J. Cell. Biochem.* L401, 1990) (ATCC VR-1110); pox viruses, such as canary pox virus or vaccinia virus (Fisher-Hoch et al., *Proc. Natl. Acad. Sci. U.S.A.* 86:317, 1989; Flexner et al., *Ann. N.Y. Acad. Sci.* 569:86, 1989; Flexner et al., *Vaccine* 8:17, 1990; U.S. Pat. No. 4,603,112 and U.S. Pat No. 4,769,330; WO 89/01973) (ATCC VR-111; ATCC VR-2010); SV40(Mulligan et al., *Nature* 277:108,1979) (ATCC VR-305), (Madzak et al., *J. Gen. Vir.* 73:1533, 1992); influenza virus (Luytjes et al., *Cell* 59:1107, 1989; McMicheal et al., *The New England Journal of Medicine* 309:13, 1983; and Yap et al., *Nature* 273:238, 1978) (ATCC VR-797); parvovirus such as adeno-associated virus (Samulski et al., *J. Vir.* 63:3822, 1989, and Mendelson et al., *Virology* 166:154, 1988) (ATCC VR-645); herpes simplex virus (Kit et al., *Adv. Exp. Med. Biol.* 215:219, 1989) (ATCC VR-977; ATCC VR-260); *Nature* 277:108, 1979); human immunodeficiency virus (EPO 386,882, Buchschacher et al., *J. Vir.* 66:2731, 1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62–33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740).

An MKK7 polynucleotide of the invention can also be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994).

In an alternative embodiment, an MKK7 polynucleotide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes. Additionally, because a liposome is a synthetic structure, specially designed liposomes can be produced which incorporate desirable features. See Stryer, *Biochemistry*, pp. 236–240, 1975 (W. H. Freeman, San Francisco, Calif.); Szoka et al., *Biochim. Biophys. Acta* 600:1, 1980; Bayer et al., *Biochim. Biophys. Acta*. 550:464, 1979; Rivnay et al., *Meth. Enzymol.* 149:119, 1987; Wang et al., *Proc. Natl. Acad. Sci. U.S.A.* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising MKK7 polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Feigner et al., *Proc. Natl. Acad. Sci. USA* 84:7413–7416, 1987), mRNA (Malone et al., *Proc. Natl. Acad. Sci. USA* 86:6077–6081, 1989), and purified transcription factors (Debs et al, *J. Biol. Chem.* 265:10189–10192, 1990), in functional form. Cationic liposomes are readily available. For example, N[1-2,3-dioleyloxy)propyl]-N,N,N- triethyl-ammonium (DOTMA) liposomes are available under the trademark Lipofectin, from GIBCO BRL, Grand Island, N.Y. See also Feigner et al., *Proc. Natl. Acad. Sci. USA* 91: 5148–5152.87, 1994. Other commercially available liposomes include Transfectace (DDAB/DOPE) and DOTAP/DOPE (Boerhinger). Other cationic liposomes can be prepared from readily available materials using techniques well known in the art. See, e.g. Szoka et al., *Proc. Natl. Acad. Sci. USA* 75:4194–4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512–527; Szoka et al., *Proc. Natl. Acad. Sci. USA* 87:3410–3414, 1990; Papahadjopoulos et al., *Biochim. Biophys. Acta* 394:483, 1975; Wilson et al., *Cell* 17:77, 1979; Deamer and Bangham, *Biochim. Biophys. Acta* 443:629, 1976; Ostro et al., *Biochem. Biophys. Res. Commun.* 76:836, 1977; Fraley et al., *Proc. Natl. Acad. Sci. USA* 76:3348, 1979; Enoch and Strittmatter, *Proc. Natl. Acad. Sci. USA* 76:145, 1979; Fraley et al., *J. Biol. Chem.* 255:10431, 1980; Szoka and Papahadjopoulos, *Proc. Natl. Acad. Sci. USA* 75:145, 1979; and Schaefer-Ridder et al., *Science* 215:166, 1982.

In addition, lipoproteins can be included with an MKK7 polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

In another embodiment, naked MKK7 polynucleotide molecules are used as gene delivery vehicles, as described in WO 90/11092 and U.S. Pat. No. 5,580,859. Such gene delivery vehicles can be either MKK7 DNA or RNA and, in certain embodiments, are linked to killed adenovirus. Curiel et al., *Hum. Gene. Ther.* 3:147–154, 1992. Other suitable vehicles include DNA-ligand (Wu et al., *J. Biol. Chem.* 264:16985–16987, 1989), lipid-DNA combinations (Felgner et al., *Proc. Natl. Acad. Sci. USA* 84:7413 7417, 1989), liposomes (Wang et al., *Proc. Natl. Acad. Sci.* 84:7851–7855, 1987) and microprojectiles (Williams et al., *Proc. Natl. Acad. Sci.* 88:2726–2730, 1991).

One can increase the efficiency of naked MKK7 polynucleotide uptake into cells by coating the polynucleotides onto biodegradable latex beads. This approach takes advantage of the observation that latex beads, when incubated with cells in culture, are efficiently transported and concentrated in the perinuclear region of the cells. The beads will then be transported into cells when injected into muscle. MKK7 polynucleotide-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of MKK7 polynucleotides into the cytoplasm.

The invention also provides a method of detecting MKK7 gene expression in a biological sample. Detection of MKK7 gene expression is useful, for example, for identifying patients who are at risk for disorders in which alterations in MKK7 gene expression or of stress-induced signal transduction via a JNK pathway are involved. Such disorders include, but are not limited to, ischemic heart disease, kidney failure, oxidative liver damage, respiratory distress syndrome, heat and radiation burns, septic shock, rheumatoid arthritis, autoimmune disorders, inflammatory processes in Alzheimer's disease, and inflammatory diseases. In patients who have been diagnosed with a condition related to MKK7 gene expression or stress-induced signal transduction through a JNK pathway, detection of levels of MKK7 expression products can be used to diagnose or prognose an MKK7-related disorder or to monitor treatment of the disorder.

The body sample can be, for example, a solid tissue or a fluid sample. The patient from whom the body sample is obtained can be healthy or can already be identified as having a condition in which altered expression of MKK7 or in which an alteration in a JNK pathway is implicated, such as those disclosed above.

Protein or nucleic acid expression products of MKK7 can be detected in the body sample. In one embodiment, the body sample is assayed for the presence of a human MKK7 protein. The MKK7 protein has the sequence shown in SEQ ID NO:2 and can be detected using the MKK7-specific antibodies. The antibodies can be labeled, for example, with a radioactive, fluorescent, biotinylated, or enzymatic tag and detected directly, or can be detected using indirect immunochemical methods, using a labeled secondary antibody. The presence of MKK7 protein can be assayed, for example, in tissue sections by immunocytochemistry, or in lysates, using Western blotting, as is known in the art.

In another embodiment, the body sample is assayed for the presence of MKK7 mRNA. MKK7 mRNA can be detected by in situ hybridization in tissue sections or in Northern blots containing poly A+ mRNA. MKK7-specific probes may be generated using the MKK7 cDNA sequence disclosed in SEQ ID NO:1. The probes are preferably 15 to 50 nucleotides in length, although they may be 8, 10, 20, 25, 30, 35, 40, 45, 60, 75, or 100 nucleotides in length. The probes can be synthesized chemically or can be generated from longer polynucleotides using restriction enzymes. The probes can be labeled, for example, with a radioactive, biotinylated, or fluorescent tag.

Optionally, the level of a particular MKK7 expression product in a body sample can be quantitated. Quantitation can be accomplished, for example, by comparing the level of expression product detected in the body sample with the amounts of product present in a standard curve. A comparison can be made visually or using a technique such as densitometry, with or without computerized assistance.

Polynucleotides encoding MKK7-specific reagents of the invention, such as antibodies and nucleotide probes, can be supplied in a kit for detecting the presence of an MKK7 expression product in a biological sample. The kit can also contain buffers or labeling components, as well as instructions for using the reagents to detect MKK7 expression products in the biological sample.

MKK7 gene expression in a cell can be increased or decreased, as desired. MKK7 gene expression can be altered for therapeutic purposes, as described below, or can be used to identify and study other components of a JNK pathway.

In one embodiment of the invention, expression of an MKK7 gene is decreased using a ribozyme, an RNA molecule with catalytic activity. See, e.g., Cech, 1987, *Science* 236: 1532–1539; Cech, 1990, *Ann. Rev. Biochem.* 59:543–568; Cech, 1992, *Curr. Opin. Struct. Biol.* 2: 605–609; Couture and Stinchcomb, 1996, *Trends Genet.* 12: 510–515. Ribozymes can be used to inhibit gene function by cleaving an RNA sequence, as is known in the art (e.g., Haseloff et al., U.S. Pat. No. 5,641,673).

The coding sequence of the MKK7 gene can be used to generate a ribozyme which will specifically bind to mRNA transcribed from a MKK7 gene. Methods of designing and constructing ribozymes which can cleave other RNA molecules in trans in a highly sequence specific manner have been developed and described in the art (see Haseloff et al., 1988, *Nature* 334:585–591). For example, the cleavage activity of ribozymes can be targeted to specific RNAs by engineering a discrete "hybridization" region into the ribozyme. The hybridization region contains a sequence complementary to the target MKK7 RNA and thus specifically hybridizes with the target (see, for example, Gerlach et al., EP 321,201). Longer complementary sequences can be used to increase the affinity of the hybridization sequence for the target. The hybridizing and cleavage regions of the MKK7 ribozyme can be integrally related; thus, upon hybridizing to the target MKK7 RNA through the complementary regions, the catalytic region of the ribozyme can cleave the target.

MKK7 ribozymes can be introduced into cells as part of a DNA construct, as is known in the art. The DNA construct can also include transcriptional regulatory elements, such as a promoter element, an enhancer or UAS element, and a transcriptional terminator signal, for controlling the transcription of the MKK7 ribozyme in the cells.

Mechanical methods, such as microinjection, liposome-mediated transfection, electroporation, or calcium phosphate precipitation, can be used to introduce the ribozyme-containing DNA construct into cells whose division it is desired to decrease, as described above. Alternatively, if it is desired that the DNA construct be stably retained by the cells, the DNA construct can be supplied on a plasmid and maintained as a separate element or integrated into the genome of the cells, as is known in the art.

As taught in Haseloff et al., U.S. Pat. No. 5,641,673, the MKK7 ribozyme can be engineered so that its expression will occur in response to factors which induce expression of the MKK7 gene. The ribozyme can also be engineered to provide an additional level of regulation, so that destruction of MKK7 mRNA occurs only when both the ribozyme and the MKK7 gene are induced in the cells.

Expression of the MKK7 gene can also be altered using an antisense oligonucleotide sequence. The antisense sequence is complementary to at least a portion of the coding sequence of a MKK7 gene having the nucleotide sequence shown in SEQ ID NO:1. The complement of the nucleotide sequence shown in SEQ ID NO:1 consists of a contiguous sequence of nucleotides which form Watson-Crick basepairs with the contiguous nucleotide sequence shown in SEQ ID NO:1.

Preferably, the antisense oligonucleotide sequence is at least six nucleotides in length, but can be about 8, 12, 15, 20, 25, 30, 35, 40, 45, or 50 nucleotides long. Longer sequences can also be used. MKK7 antisense oligonucleotide molecules can be provided in a DNA construct and introduced into cells whose division is to be decreased, as described above.

MKK7 antisense oligonucleotides can be composed of deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, *Meth. Mol. Biol.* 20:1–8; Sonveaux, 1994, *Meth. Mol. Biol.* 26:1–72; Uhlmann et al., 1990, *Chem. Rev.* 90:543–583.

Although precise complementarity is not required for successful duplex formation between an MKK7 antisense molecule and the complementary coding sequence of an MKK7 gene, antisense molecules with no more than one mismatch are preferred. One skilled in the art can easily use the calculated melting point of an MKK7 antisense-sense pair to determine the degree of mismatching which will be tolerated between a particular antisense oligonucleotide and a particular MKK7 coding sequence of the selected gene.

MKK7 antisense oligonucleotides can be modified without affecting their ability to hybridize to a MKK7 coding sequence. These modifications can be internal or at one or both ends of the antisense molecule. For example, intemucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, can also be employed in a modified antisense oligonucleotide. These modified oligonucleotides can be prepared by methods well known in the art. Agrawal et al., 1992, *Trends Biotechnol.* 10:152–158; Uhlmann et al., 1990, *Chem. Rev.* 90:543–584; Uhlmann et al., 1987, *Tetrahedron. Lett.* 215:3539–3542.

Antibodies which specifically bind to an MKK7 protein can also be used to alter MKK7 gene expression. MKK7-specific antibodies bind to MKK7 protein and prevent the protein from functioning in the cell. Polynucleotides encoding MKK7-specific antibodies can be introduced into cells, as described above.

To increase MKK7 gene expression, all or a portion of an MKK7 gene or expression product can be introduced into a cell. Optionally, the gene or expression product can be a component of a therapeutic composition comprising a pharmaceutically acceptable carrier (see below). The entire MKK7 coding sequence can be introduced, as described above. Alternatively, a portion of the MKK7 protein which is capable of phosphorylating a JNK substrate can be identified and that portion or a nucleotide sequence encoding it can be introduced into the cell. Portions of MKK7 protein which phosphorylate JNK can be identified by introducing expression constructs which express different portions of the protein into cells and assaying MKK7 kinase activity, as described above.

MKK7 protein or a portion of an MKK7 protein can also be used to alter transcription of a gene responsive to an AP-1 transcription factor. AP-1 transcription factors comprise proteins such as ATF2, c-Jun, c-fos, JurB, JunD, Fos B, Fra-1, Fra-2, and ATF/CREB, which are phosphorylated by a c-Jun $NH_2$ terminal kinase. Thus, the degree to which a c-Jun $NH_2$ terminal kinase, such as JNK1 ($p54_\gamma$), JNK2 ($p54_\alpha$), or JNK3 ($p54^\beta$), is phosphorylated can be used to alter transcription of genes which are responsive to AP-1 transcription factors.

Genes whose transcription can be regulated include those genes which are naturally responsive to AP-1 factors, such as the CD11c leukocyte integrin gene. Transcription of genes which have been placed under the control of an AP-1 factor using standard recombinant DNA techniques, can also be controlled using this approach.

Gene transcription can be either increased or decreased. To increase transcription of an AP-1-responsive gene, a cell comprising the gene to be regulated is contacted with a polynucleotide encoding all or a portion of an MKK7 protein. The step of contacting can be carried out either in vitro, using methods described above, or in vivo, using methods described below.

The step of contacting is carried out under conditions where MKK7 protein or portion of the MKK7 protein phosphorylates a c-Jun $NH_2$-terminal kinase. The c-Jun $NH_2$-terminal kinase is a kinase such as JNK1 ($p54_\gamma$), JNK2 ($p54_\alpha$) or JNK3 ($p54^\beta$). The conditions under which such kinases are phosphorylated are described, for example, in Tournier et al., 1997, *Proc. Natl. Acad. Sci. USA* 94:7337–42, and WO 96/36642. Phosphorylation of the c-Jun $NH_2$-terminal kinase phosphorylates an AP-1 transcription factor, thereby increasing transcription of the AP-1-responsive gene.

To decrease transcription of an AP-1-responsive gene, a cell is contacted with a polynucleotide encoding a reagent which binds to an MKK7 gene or expression product. Such reagents can be, for example, antibodies, ribozymes, and MKK7 antisense oligonucleotides. The ability of MKK7 protein to phosphorylate a c-Jun $NH_2$-terminal kinase is decreased in the presence of one or more of these reagents, as disclosed above.

The invention also provides a method to identify test compounds which modulate JNK stress-inducted signal transduction pathways. A test compound can be a pharmacologic agent already known in the art or can be a compound previously unknown to have any pharmacological activity. The compound can be naturally occurring or designed in the laboratory. It can be isolated from microorganisms, animals, or plants, and can be produced recombinantly, or synthesized by chemical methods known in the art.

Test compounds which modulate signal transduction through a JNK pathway can be used to enhance or decrease cellular responses to stress mediated through the JNK pathway. A test compound which enhances signal transduction through the JNK pathway can be used, for example, to decrease or prevent apoptosis in diseases in which cell death occurs, such as heart attack and stroke. A test compound which decreases signal transduction through the JNK pathway can be used, for example, to induce or increase apoptosis, for treatment of diseases such as neoplasia.

Such test compounds can be identified by their effect on the phosphorylation of MKK7, MKK7 synthesis, or MKK7 activity. Phosphorylation of MKK7 or MKK7 synthesis or activity in the presence or absence of a test compound can be measured in a biological sample. The biological sample can be whole cells or extracts of human cells which express MKK7, such as heart, brain, lung, liver, muscle, kidney, or testis, or in whole cells or extracts of human cell lines. A variety of cell lines are commercially available or can be obtained from the ATCC for this purpose. Assays for phosphorylation of MAP kinase kinases are taught, for example, in Tournier et al., 1997.

The effect of a test compound on MKK7 synthesis can also be used to identify test compounds which modulate stress-induced signal transduction through JNK pathways. Synthesis of MKK7 can be measured by any means for measuring protein synthesis known in the art, such as incorporation of labeled amino acids into proteins and detection of labeled MKK7 protein in a polyacrylamide gel. The amount of MKK7 protein can be detected, for example, using MKK7-specific antibodies in Western blots. The amount of MKK7 protein synthesized in the presence or absence of a test compound can be determined by any means known in the art, such as comparison of the amount of MKK7 synthesized with the amount of MKK7 protein present in a standard curve.

The effect of a test compound on MKK7 synthesis can also be measured by Northern blot analysis, by measuring the amount of MKK7 mRNA expression in response to the test compound using MKK7 specific nucleotide probes of the invention, as is known in the art.

MKK7 activity can be measured using in vitro kinase assays, as described in WO 96/36642. For identifying a test substance which modulates MKK7 activity, a kinase assay can be carried out using an MKK7 substrate, and a radioactive marker such as [$\gamma$-$32^P$]ATP. The substrate can be, for example, a c-Jun NH2-terminal kinase, such as JNK1 ($p54_\gamma$), JNK2 ($p54_\alpha$), or JNK3 ($p54^\beta$).

Typically, the biological sample is contacted with a range of concentrations of the test compound, such as 1.0 nM, 5.0 nM, 10 nM, 50 nM, 100 nM, 500 nM, 1 mM, 10 mM, 50 mM, and 100 mM. Preferably, the test compound increases or decreases phosphorylation of MKK7 or MKK7 synthesis or activity by 60%, 75%, or 80%. More preferably, an increase or decrease of 85%, 90%, 95%, or 98% is achieved.

The invention provides therapeutic compositions for increasing or decreasing expression of MKK7. Increasing MKK7 gene expression is useful, for example, for treating diseases in which, for example, increased apoptosis is desired, such as neoplasia, hyperplasia, and dysplasia. Therapeutic compositions for increasing MKK7 gene expression comprise polynucleotides encoding all or a portion of an MKK7 expression product. Preferably, the therapeutic composition contains an expression construct comprising a promoter and a polynucleotide segment encoding at least six contiguous amino acids of MKK7 protein. Within the expression construct, the polynucleotide segment is located downstream from the promoter, and transcription of the polynucleotide segment initiates at the promoter. A more complete description of gene transfer vectors, especially retroviral vectors is contained in U.S. Ser. No. 08/869,309.

Decreased MKK7 gene expression is desired in conditions in which decreased apoptosis is desired, for example, ischemic heart disease, kidney failure, septic shock, and stroke. Therapeutic compositions for treating these disorders comprise a polynucleotide encoding a reagent which specifically binds to an MKK7 expression product, as disclosed herein.

MKK7 therapeutic compositions of the invention also comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates.

Therapeutic compositions can also contain liquids, such as water, saline, glycerol, and ethanol, as well as substances such as wetting agents, emulsifying agents, or pH buffering agents. Liposomes, such as those described in U.S. Pat No. 5,422,120, WO 95/13796, WO 91/14445, or EP 524,968 B1, can also be used as a carrier for the therapeutic MKK7 composition.

Typically, a therapeutic MKK7 composition is prepared as an injectable, either as a liquid solution or suspension; however, solid forms suitable for solution in, or suspension in, liquid vehicles prior to injection can also be prepared. A MKK7 composition can also be formulated into an enteric coated tablet or gel capsule according to known methods in the art, such as those described in U.S. Pat. No. 4,853,230, EP 225,189, AU 9,224,296, and AU 9,230,801.

Administration of the MKK7 therapeutic agents of the invention can include local or systemic administration, including injection, oral administration, particle gun, or catheterized administration, and topical administration. Various methods can be used to administer a therapeutic MKK7 composition directly to a specific site in the body.

For treatment of tumors, for example, a small tumor or metastatic lesion can be located and a therapeutic MKK7 composition injected several times in several different locations within the body of tumor. Alternatively, arteries which serve a tumor can be identified, and a therapeutic composition injected into such an artery, in order to deliver the composition directly into the tumor.

A tumor which has a necrotic center can be aspirated and the composition injected directly into the now empty center of the tumor. A therapeutic MKK7 composition can be directly administered to the surface of a tumor, for example, by topical application of the composition. X-ray imaging can be used to assist in certain of the above delivery methods. Combination therapeutic agents, including an MKK7 protein or polypeptide or MKK7 subgenomic polynucleotide and other therapeutic agents, can be administered simultaneously or sequentially.

Receptor-mediated targeted delivery can be used to deliver therapeutic compositions containing MKK7 subgenomic polynucleotides, proteins, or reagents such as antibodies, ribozymes, or antisense oligonucleotides to specific tissues. Receptor-mediated delivery techniques are described in, for example, Findeis et al. (1993), *Trends in Biotechnol.* 11, 202–05; Chiou et al. (1994), GENE THERAPEUTICS: METHODS AND APPLICATIONS OF DIRECT GENE TRANSFER (J. A. Wolff, ed.); Wu & Wu (1988), *J. Biol. Chem.* 263, 621–24; Wu et al. (1994), *J. Biol. Chem.* 269, 54246; Zenke et al. (1990), *Proc. Natl. Acad. Sci. U.S.A.* 87, 3655–59; Wu et al. (1991), *J. Biol. Chem.* 266, 338–42.

Alternatively, an MKK7 therapeutic composition can be introduced into human cells ex vivo, and the cells then replaced into the human. Cells can be removed from a variety of locations including, for example, from a selected tumor or from an affected organ. In addition, a therapeutic composition can be inserted into non-affected, for example, dermal fibroblasts or peripheral blood leukocytes. If desired, particular fractions of cells such as a T cell subset or stem cells can also be specifically removed from the blood (see, for example, PCT WO 91/16116): The removed cells can then be contacted with an MKK7 therapeutic composition utilizing any of the above-described techniques, followed by the return of the cells to the human, preferably to or within the vicinity of a tumor or other site to be treated. The methods described above can additionally comprise the steps of depleting fibroblasts or other non-contaminating tumor cells subsequent to removing tumor cells from a human, and/or the step of inactivating the cells, for example, by irradiation.

Both the dose of an MKK7 composition and the means of administration can be determined based on the specific qualities of the therapeutic composition, the condition, age, and weight of the patient, the progression of the disease, and other relevant factors. Preferably, a therapeutic composition of the invention increases or decreases expression of the MKK7 gene by 50%, 60%, 70%, or 80%. Most preferably, expression of the MKK7 gene is increased or decreased by 90%, 95%, 99%, or 100%. The effectiveness of the mechanism chosen to alter expression of the MKK7 gene can be assessed using methods well known in the art, such as hybridization of nucleotide probes to mRNA of the MKK7 gene, quantitative RT-PCR, or detection of an MKK7 protein using specific antibodies.

If the composition contains MKK7 protein, polypeptide, or antibody, effective dosages of the composition are in the range of about 5 $\mu$g to about 50 $\mu$g/kg of patient body weight, about 50 $\mu$g to about 5 mg/kg, about 100 $\mu$g to about 500 $\mu$g/kg of patient body weight, and about 200 to about 250 $\mu$g/kg.

Therapeutic compositions containing MKK7 subgenomic polynucleotides can be administered in a range of about 100 ng to about 200 mg of DNA for local administration in a gene therapy protocol. Concentration ranges of about 500 ng to about 50 mg, about 1 $\mu$g to about 2 mg, about 5 pg to about 500 $\mu$g, and about 20 $\mu$g to about 100 $\mu$g of DNA can also be used during a gene therapy protocol. Factors such as method of action and efficacy of transformation and expression are considerations that will effect the dosage required for ultimate efficacy of the MKK7 subgenomic polynucleotides, Where greater expression is desired over a larger area of tissue, larger amounts of MKK7 subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect.

Expression of an endogenous MKK7 gene in a cell can also be altered by introducing in frame with the endogenous MKK7 gene a DNA construct comprising an MKK7 targeting sequence, a regulatory sequence, an exon, and an unpaired splice donor site by homologous recombination, such that a homologously recombinant cell comprising the DNA construct is formed. The new transcription unit can be used to turn the MKK7 gene on or off as desired. This method of affecting endogenous gene expression is taught in U.S. Pat. No. 5,641,670.

The targeting sequence is a segment of at least 10, 12, 15, 20, or 50 contiguous nucleotides selected from the nucleotide sequence shown in SEQ ID NO:1. The transcription unit is located upstream of a coding sequence of the endogenous MKK7 gene. The exogenous regulatory sequence directs transcription of the coding sequence of the MKK7 gene.

The invention provides knock-out mammals whose endogenous MKK7 gene is not expressed. Methods of making knock-out mammals are well known in the art. The mammal can be any experimental mammal, such as a mouse, rat, or rabbit; however, a mouse is preferred. The endogenous wild-type MKK7 gene of the mammal can be deleted entirely, resulting in an absence of MKK7 protein in the mammal. Alternatively, mutations such as deletions, insertions, missense substitutions, or inversions, can be introduced into the MKK7 gene. Such mutations result in expression of truncated or otherwise aberrant forms of MKK7 protein in the knock-out mammal. Mammalian cell lines which do not express an endogenous MKK7 gene can also be constructed, as is known in the art.

Knock-out mammals and cells of the invention are useful as model systems for studying the effects of drugs in the absence of wild-type MKK7 protein or in the presence of altered forms of the MKK7 protein in the mammal or cell. Knock-out mammals can also be used to develop therapeutic treatments for diseases associated with alterations in MKK7 gene expression, such as ischemic heart disease, kidney failure, oxidative liver damage, respiratory distress syndrome, heat and radiation burns, septic shock, rheumatoid arthritis, autoimmune disorders, and inflammatory diseases.

An MKK7 subgenomic polynucleotide can also be delivered to subjects for the purpose of screening test compounds for those which are useful for enhancing transfer of MKK7 subgenomic polynucleotides to the cell or for enhancing subsequent biological effects of MKK7 subgenomic polynucleotides within the cell. Such biological effects include hybridization to complementary MKK7 mRNA and inhibition of its translation, expression of an MKK7 subgenomic polynucleotide to form an MKK7 mRNA, single-chain antibody, ribozyme, oligonucleotide, or protein and/or replication and integration of an MKK7 subgenomic polynucleotide. The subject can be a cell culture or an animal, preferably a mammal, more preferably a human.

Test compounds which can be screened include any substances, whether natural products or synthetic, which can be administered to the subject in vitro or in vivo. Libraries or mixtures of test compounds can be tested. The test compound can be a pharmacologic agent already known in the art or can be a compound previously unknown to have any pharmacological activity. The test compound can be naturally occurring or designed in the laboratory. It can be isolated from microorganisms, animals, or plants, and can be produced recombinantly, or synthesized by chemical methods known in the art. Test compounds or substances can be delivered before, after, or concomitantly with an MKK7 subgenomic polynucleotide. They can be administered separately or in admixture with an MKK7 subgenomic polynucleotide.

Integration of a delivered MKK7 subgenomic polynucleotide can be monitored by any means known in the art. For example, Southern blotting of the delivered MKK7 subgenomic polynucleotide can be performed. A change in the size of the fragments of a delivered polynucleotide indicates integration. Replication of a delivered polynucleotide can be monitored inter alia by detecting incorporation of labeled nucleotides combined with hybridization to an MKK7 probe. Expression of an MKK7 subgenomic polynucleotide can be monitored by detecting production of MKK7 mRNA which hybridizes to the delivered polynucleotide or by. detecting MKK7 protein. MKK7 protein can be detected immunologically. Thus, the delivery of MKK7 subgenomic polynucleotides according to the present invention provides an excellent system for screening test compounds for their ability to enhance transfer of MKK7 polynucleotides to a cell, by enhancing delivery, integration, hybridization, expression, replication or integration in a cell in vitro or in vivo in an animal, preferably a mammal, more preferably a human.

The complete contents of the references cited in this disclosure are expressly incorporated by reference herein.

What is claimed is:

1. A method of identifying a test compound which modulates signal transduction through a JNK pathway, comprising the steps of:

contacting a biological sample with a test compound; and detecting phosphorylation or synthesis of an MKK7 protein as shown in SEQ ID NO:2, wherein a test compound which increases or decreases phosphorylation or synthesis of the MKK7 protein identifies a potential drug for modulating signal transduction through the JNK pathway.

2. The method of claim 1 wherein the synthesis of said MKK7 protein is detected by:

a) incorporating labeled amino acids into said MKK7 protein; and b) detecting labeled MKK7 protein.

3. The method of claim 1 wherein the synthesis of said MKK7 protein is detected by:

a) contacting said MKK7 protein with an MKK7-specific antibody; and b) detecting the formation of protein-antibody complexes.

4. The method of claim 1 wherein the synthesis of said MKK7 protein is detected by measuring the amount of MKK7 mRNA expression in response to said test compound.

* * * * *

SEQUENCE LISTING

<160> NUMBER OF SEQ ID NOS: 9

<210> SEQ ID NO 1
<211> LENGTH: 1260
<212> TYPE: DNA
<213> ORGANISM: Homo sapien

<400> SEQUENCE: 1

```
atggcggcgt cctccctgga acagaagctg tcccgcctgg aagcaaagct gaagcaggag      60
aaccgggagg cccggcggag gatcgacctc aacctggata tcagccccca gcggcccagg     120
cccaccctgc agctcccgct ggccaacgat gggggcagcc gctcgccatc ctcagagagc     180
tccccgcagc accccacgcc ccccgcccgg ccccgccaca tgctggggct cccgtcaacc     240
ctgttcacac cccgcagcat ggagagcatt gagattgacc agaagctgca ggagatcatg     300
aagcagacgg gctacctgac catcggggc cagcgctacc aggcagaaat caacgacctg     360
gagaacttgg gcgagatggg cagcggcacc tgcggccagg tgtggaagat gcgcttccgg     420
aagaccggcc acgtcattgc cgttaagcaa atgcggcgct ccgggaacaa ggaggagaac     480
aagcgcatcc tcatggacct ggatgtggtg ctgaagagcc acgactgccc ctacatcgtg     540
cagtgctttg ggacgttcat caccaacacg gacgtcttca tcgccatgga gctcatgggc     600
acctgcgctg agaagctcaa gaagcggatg cagggcccca tccccgagcg cattctgggc     660
aagatgacag tggcgattgt gaaggcgctg tactacctga aggagaagca cggtgtcatc     720
caccgcgacg tcaagccctc caacatcctg ctggacgagc ggggccagat caagctctgc     780
```

-continued

```
gacttcggca tcagcggccg cctggtggac tccaaagcca agacgcggag cgccggctgt    840
gccgcctaca tggcacccga gcgcattgac ccccagacc ccaccaagcc ggactatgac      900 atccggggccg acgtatggag cctgggcatc tcgttggtgg agctggcaac aggacagttt    960
ccctacaaga actgcaagac ggactttgag gtcctcacca aagtcctaca ggaagagccc   1020
ccgcttctgc ccggacacat gggcttctcg ggggacttcc agtccttcgt caaagactgc   1080
cttactaaag atcacaggaa gagaccaaag tataataagc tacttgaaca cagcttcatc   1140
aagcgctacg agacgctgga ggtggacgtg gcgtcctggt tcaaggatgt catggcgaag   1200
actgagtcac cgcggactag cggcgtcctg agccagcccc acctgcccctt cttcaggtag  1260
```

<210> SEQ ID NO 2
<211> LENGTH: 419
<212> TYPE: PRT
<213> ORGANISM: Homo sapien

<400> SEQUENCE: 2

```
Met Ala Ala Ser Ser Leu Glu Gln Lys Leu Ser Arg Leu Glu Ala Lys
 1               5                  10                  15

Leu Lys Gln Glu Asn Arg Glu Ala Arg Arg Arg Ile Asp Leu Asn Leu
            20                  25                  30

Asp Ile Ser Pro Gln Arg Pro Arg Pro Thr Leu Gln Leu Pro Leu Ala
        35                  40                  45

Asn Asp Gly Gly Ser Arg Ser Pro Ser Ser Glu Ser Ser Pro Gln His
    50                  55                  60

Pro Thr Pro Pro Ala Arg Pro Arg His Met Leu Gly Leu Pro Ser Thr
65                  70                  75                  80

Leu Phe Thr Pro Arg Ser Met Glu Ser Ile Glu Ile Asp Gln Lys Leu
                85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
        115                 120                 125

Gly Thr Cys Gly Gln Val Trp Lys Met Arg Phe Arg Lys Thr Gly His
    130                 135                 140

Val Ile Ala Val Lys Gln Met Arg Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
        195                 200                 205

Arg Met Gln Gly Pro Ile Pro Glu Arg Ile Leu Gly Lys Met Thr Val
    210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
        275                 280                 285

Ile Asp Pro Pro Asp Pro Thr Lys Pro Asp Tyr Asp Ile Arg Ala Asp
```

```
            290                 295                 300
Val Trp Ser Leu Gly Ile Ser Leu Val Glu Leu Ala Thr Gly Gln Phe
305                 310                 315                 320

Pro Tyr Lys Asn Cys Lys Thr Asp Phe Glu Val Leu Thr Lys Val Leu
                325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
        355                 360                 365

Pro Lys Tyr Asn Lys Leu Leu Glu His Ser Phe Ile Lys Arg Tyr Glu
    370                 375                 380

Thr Leu Glu Val Asp Val Ala Ser Trp Phe Lys Asp Val Met Ala Lys
385                 390                 395                 400

Thr Glu Ser Pro Arg Thr Ser Gly Val Leu Ser Gln Pro His Leu Pro
                405                 410                 415

Phe Phe Arg

<210> SEQ ID NO 3
<211> LENGTH: 1775
<212> TYPE: DNA
<213> ORGANISM: Homo sapien

<400> SEQUENCE: 3
aggccaagaa ttcggcacga ggcttgattt gcatgcaaca cccacaaaaa ggaaacacac     60
cccctcctgc tctggccacc ccagcaggct ccggggggca cctggcctgg gtccccggtg    120
cactcacccg gtccttccca gtcctggacc tcaacgtgga ctgggccagg tgtgggtgag    180
tggagggacg gccaggggca cgatgggagt gaccacctcg cacccccacc ctcagcccgg    240
cccccacccc tgctggagct tgtcacacgt cctcaaaccc ccacatccac tccctctgcc    300
ctccatccct gactccctcc ggacccctcc cttggccccc gctccgtcac cgattccctc    360
cggtcacctg ctgtgcacca tgccccaaga ccaccttccc tgaaggccat cctgtgcggc    420
cagggccccg cagacccctc cacatcccct gaggtcttca actcacccca gctgtggcc    480 cccggagacc ccagagcagc agccccagcc cagctcccca gtgcccgagg cggttgggg    540 ccccaccaca agcagctaat cgtgactttg gtaaaagttt ctgaaggtac cgacaacccc    600
acgagaacaa gctctcctcc gcccccaccc caaacacccc accaagtaca ataaaataca    660
ataaactcca aaaggacccc ctgagatca aagagagaga gagagagaga gagagagcgc    720
gagcgcgcag ccccgtccag ccgcagtggc aatgcccaca ctgcctggct gggggccact    780
gactcattgc gccatgggag acctatgcag acccagggga cccgtcagga ggtggctggg    840
cccaggctca ggccagaaga gagacagagg cagggagggt gacggagagc ccagacaagg    900
acagagaggt agagcagggg acagagggcg acggaagagg aacgggcgcg tgggagtggc    960
gaaggacaca gcacgctggg agcgtgcatg gtggctgcgg gactccaggg ctctctcctg   1020
gcccctgggg gccgccccgg cccagaggct gcggctgaat aacagcgac tctgatcgcg    1080 gcctgctgtc ttccgttcac agtgtctgtc ggggacgca cacggccggc tgaccccggg    1140
gtgggaaggg cggggggggt gggtgggcac ccccactct ctgtcctcag tcctaggtgg   1200
ccgtccaggt cccaggtctc cctggcagg cagctgggtg gccaagtggg gagggggcc    1260 tgtggccatg cccctggccc cctgtgggg ctggccgccg ccaagcagct acctgaagaa    1320
gggcaggtgg ggctggctca ggacgccgct agtccgcggt gactcagtct tcgccatgac   1380
```

-continued

```
atccttgaac caggacgcca cgtccacctc cagcgtctcg tagcgcttga tgaagctgtg    1440
ttcaagtagc ttattatact ttggtctctt cctgtgatct ttagtaaggc agtctttgac    1500
gaaggactgg aagtcccccg agaagcccat gtgtccgggc agaagcgggg gctcttcctg    1560
taggactttg gtgaggacct caaagtccgt cttgcagttc ttgtagggaa actgtcctgt    1620
tgccagctcc accaacgaga tgcccaggct ccatacgtcg gcccggatgt catagtccgg    1680
cttggtgggg tctgggggt caatgcgctc gggtgccatg taggcggcac agccggcgct    1740
ccgcgtcttg gctttggagt ccaccaggcg ccgc                                1775

<210> SEQ ID NO 4
<211> LENGTH: 906
<212> TYPE: DNA
<213> ORGANISM: Homo sapien

<400> SEQUENCE: 4
gcggccgctg atgccgaagt cgcagagctt gatctggccc cgctcgtcca gcaggatgtt     60
ggagggcttg acgtcgcggt ggatgacacc gtgcttctcc ttcaggtagt acagcgcctt    120
cacaatcgcc actgtcatct tgcccagaat gcgctcgggg atgggccct gcatccgctt    180 cttgagcttc tcagcgcagg tgcccatgag ctccatggcg atgaagacgt ccgtgttggt    240
gatgaacgtc ccaaagcact gcacgatgta ggggcagtcg tggctcttca gcaccacatc    300
caggtccatg aggatgcgct tgttctcctc cttgttcccg gagcgccgca tttgcttaac    360
ggcaatgacg tggccggtct ccggaagcg catcttccac acctggccgc aggtgccgct    420
gcccatctcg cccaagttct ccaggtcgtt gatttctgcc tggtagcgct ggccccgat    480 ggtcaggtag cccgtctgct tcatgatctc ctgcagcttc tggtcaatct caatgctctc    540
catgctgcgg ggtgtgaaca gggttgacgg gagccccagc atgtggcggg gccgggcggg    600
gggcgtgggg tgctgcgggg agctctctga ggatggcgag cggctgcccc catcgttggc    660
cagcgggagc tgcagggtgg gcctgggccg ctggggctg atatccaggt tgaggtcgat    720
cctccgccgg gcctccggt tctcctgctt cagctttgct tccaggcggg acagcttctg    780
ttccagggag gacgccgcca tcttccccgc cgccaccgcc gccgcgcacc gcccggccgc    840
ccgtcagtcc ggcagacaaa cacctcgtgc cgaattcttg gcctcgaggg ccaaattccc    900
tatagt                                                               906

<210> SEQ ID NO 5
<211> LENGTH: 419
<212> TYPE: PRT
<213> ORGANISM: Mus musculus

<400> SEQUENCE: 5

Met Ala Ala Ser Ser Leu Glu Gln Lys Leu Ser Arg Leu Glu Ala Lys
 1               5                  10                  15

Leu Lys Gln Glu Asn Arg Glu Ala Arg Arg Arg Ile Asp Leu Asn Leu
                20                  25                  30

Asp Ile Ser Pro Gln Arg Pro Arg Pro Thr Leu Gln Leu Pro Leu Ala
            35                  40                  45

Asn Asp Gly Gly Ser Arg Ser Pro Ser Ser Glu Ser Ser Pro Gln His
        50                  55                  60

Pro Thr Pro Pro Thr Arg Pro Arg His Met Leu Gly Leu Pro Ser Thr
65                  70                  75                  80

Leu Phe Thr Pro Arg Ser Met Glu Ser Ile Glu Ile Asp Gln Lys Leu
                85                  90                  95
```

```
Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
            115                 120                 125

Gly Thr Cys Gly Gln Val Trp Lys Met Arg Phe Arg Lys Thr Gly His
            130                 135                 140

Ile Ile Ala Val Lys Gln Met Arg Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
            195                 200                 205

Arg Met Gln Gly Pro Ile Pro Glu Arg Ile Leu Gly Lys Met Thr Val
            210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
            275                 280                 285

Ile Asp Pro Pro Asp Pro Thr Lys Pro Asp Tyr Asp Ile Arg Ala Asp
            290                 295                 300

Val Trp Ser Leu Gly Ile Ser Leu Val Glu Leu Ala Thr Gly Gln Phe
305                 310                 315                 320

Pro Tyr Lys Asn Cys Lys Thr Asp Phe Glu Val Leu Thr Lys Val Leu
                325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
            355                 360                 365

Pro Lys Tyr Asn Lys Leu Leu Glu His Ser Phe Ile Lys His Tyr Glu
            370                 375                 380

Ile Leu Glu Val Asp Val Ala Ser Trp Phe Lys Asp Val Met Ala Lys
385                 390                 395                 400

Thr Glu Ser Pro Arg Thr Ser Gly Val Leu Ser Gln His His Leu Pro
                405                 410                 415

Phe Phe Arg

<210> SEQ ID NO 6
<211> LENGTH: 487
<212> TYPE: PRT
<213> ORGANISM: Drosophilia melanogaster

<400> SEQUENCE: 6

Met Ser Thr Ile Glu Phe Glu Thr Ile Gly Ser Arg Leu Gln Ser Leu
1               5                   10                  15

Glu Ala Lys Leu Gln Ala Gln Asn Glu Ser His Asp Gln Ile Val Leu
            20                  25                  30

Ser Gly Ala Arg Gly Pro Val Val Ser Gly Ser Val Pro Ser Ala Arg
            35                  40                  45
```

-continued

```
Val Pro Pro Leu Ala Thr Ser Ala Ser Ala Ala Thr Ser Ala Thr His
    50                  55                  60
Ala Pro Ser Leu Gly Ala Ser Ser Val Ser Gly Ser Gly Ile Ser Ile
65                  70                  75                  80
Ala Gln Arg Pro Ala Pro Val Pro His Ala Thr Leu Arg Ser Pro
            85                  90                  95
Ser Ala Ser Ser Ser Ser Ser Arg Ser Ala Phe Arg Ser Ala Ala
                100                 105                 110
Pro Ala Thr Gly Leu Arg Trp Thr Tyr Thr Pro Thr Thr Arg Val
        115                 120                 125
Ser Arg Ala Thr Pro Thr Leu Pro Met Leu Ser Ser Gly Pro Gly Gly
    130                 135                 140
Asp Val Glu Cys Thr Arg Pro Val Ile Leu Pro Leu Pro Thr Pro Pro
145                 150                 155                 160
His Pro Pro Val Ser Glu Thr Asp Met Lys Leu Lys Ile Ile Met Glu
                165                 170                 175
Gln Thr Gly Lys Leu Asn Ile Asn Gly Arg Gln Tyr Pro Thr Asp Ile
            180                 185                 190
Asn Asp Leu Lys His Leu Gly Asp Leu Gly Asn Gly Thr Ser Gly Asn
                195                 200                 205
Val Val Lys Met Met His Leu Ser Ser Asn Thr Ile Ile Ala Val Lys
    210                 215                 220
Gln Met Arg Arg Thr Gly Asn Ala Glu Glu Asn Lys Arg Ile Leu Met
225                 230                 235                 240
Asp Leu Asp Val Val Leu Lys Ser His Asp Cys Lys Tyr Ile Val Lys
                245                 250                 255
Cys Leu Gly Cys Phe Val Arg Asp Pro Asp Val Trp Ile Cys Met Glu
            260                 265                 270
Leu Met Ser Met Cys Phe Asp Lys Leu Leu Lys Leu Ser Lys Lys Pro
        275                 280                 285
Val Pro Glu Gln Ile Leu Gly Lys Val Thr Val Ala Thr Val Asn Ala
    290                 295                 300
Leu Ser Tyr Leu Lys Asp Lys His Gly Val Ile His Arg Asp Val Lys
305                 310                 315                 320
Pro Ser Asn Ile Leu Ile Asp Glu Arg Gly Asn Ile Lys Leu Cys Asp
                325                 330                 335
Phe Gly Ile Ser Gly Arg Leu Val Asp Ser Lys Ala Asn Thr Arg Ser
            340                 345                 350
Ala Gly Cys Ala Ala Tyr Met Ala Pro Glu Arg Ile Asp Pro Lys Lys
        355                 360                 365
Pro Lys Tyr Asp Ile Arg Ala Asp Val Trp Ser Leu Gly Ile Thr Leu
    370                 375                 380
Val Glu Leu Ala Thr Ala Arg Ser Pro Tyr Glu Gly Cys Asn Thr Asp
385                 390                 395                 400
Phe Glu Val Leu Thr Lys Val Leu Asp Ser Glu Pro Pro Cys Leu Pro
                405                 410                 415
Tyr Gly Glu Gly Tyr Asn Phe Ser Gln Gln Phe Arg Asp Phe Val Ile
            420                 425                 430
Lys Cys Leu Thr Lys Asn His Gln Asp Arg Pro Lys Tyr Pro Glu Leu
        435                 440                 445
Leu Ala Gln Pro Phe Ile Arg Ile Tyr Glu Ser Ala Lys Val Asp Val
    450                 455                 460
```

| Pro Asn Trp Phe Gln Ser Ile Lys Asp Asn Asp Cys Gly Gln Trp Arg |
| 465 470 475 480 |

Ser Asn Ala Pro Glu Val Thr
            485

<210> SEQ ID NO 7
<211> LENGTH: 1260
<212> TYPE: DNA
<213> ORGANISM: Mus musculus

<400> SEQUENCE: 7

| atggcggcgt cctccctgga gcagaagctg tcccgcctgg aagccaagct gaagcaggag | 60 |
| aaccgtgagg cccgcaggag gatcgacctc aacttggata tcagcccaca gcggcccagg | 120 |
| cccacccctgc aactcccact ggccaacgat gggggcagcc gctcaccatc ctcagagagc | 180 |
| tccccacagc accctacacc ccccaccccgg ccccgccaca tgctggggct cccatcaacc | 240 |
| ttgttcacac cgcgcagtat ggagagcatc gagattgacc agaagctgca ggagatcatg | 300 |
| aagcagacag gtacctgac tatcgggggc cagcgttatc aggcagaaat caatgacttg | 360 |
| gagaacttgg gtgagatggg cagtggtacc tgtggtcagg tgtggaagat gcggttccgg | 420 |
| aagacaggcc acatcattgc tgttaagcaa atgcggcgct ctgggaacaa ggaagagaat | 480 |
| aagcgcattt tgatggacct ggatgtagta ctcaagagcc atgactgccc ttacatcgtt | 540 |
| cagtgctttg gcaccttcat caccaacaca gacgtcttta ttgccatgga gctcatgggc | 600 |
| acatgtgcag agaagctgaa gaaacgaatg cagggccccca ttccagagcg aatcctgggc | 660 |
| aagatgactg tggcgattgt gaaagcactg tactatctga aggagaagca tggcgtcatc | 720 |
| catcgcgatg tcaaaccctc caacatcctg ctagatgagc ggggccagat caagctctgt | 780 |
| gactttggca tcagtggccg tcttgttgac tccaaagcca aaacacggag tgctggctgt | 840 |
| gctgcctata tggctcccga gcgcatcgac cctccagatc ccaccaagcc tgactatgac | 900 |
| atccgagctg atgtgtggag cctgggcatc tcactggtgg agctggcaac aggacagttc | 960 |
| ccctataaga actgcaagac ggactttgag gtcctcacca agtcctaca ggaagagccc | 1020 |
| ccactcctgc ctggtcacat gggcttctca ggggacttcc agtcatttgt caaagactgc | 1080 |
| cttactaaag atcacaggaa gagaccaaag tataataagc tacttgaaca cagtttcatc | 1140 |
| aagcactatg agatactcga ggtggatgtc gcgtcctggt ttaaggatgt catggcgaag | 1200 |
| accgagtccc caaggactag tggagtcctg agtcagcacc atctgccctt cttcaggtag | 1260 |

<210> SEQ ID NO 8
<211> LENGTH: 1260
<212> TYPE: DNA
<213> ORGANISM: Homo sapien

<400> SEQUENCE: 8

| taccgccgca ggagggacct tgtcttcgac agggcggacc ttcgtttcga cttcgtcctc | 60 |
| ttggcccctcc gggccgcctc ctagctggag ttggacctat agtcgggggt cgccgggtcc | 120 |
| gggtgggacg tcgagggcga ccggttgcta ccccgtcgg cgagcggtag gagtctctcg | 180 |
| agggcgtcg tggggtgcgg ggggcgggcc ggggcggtgt acgacccccga ggcagttgg | 240 |
| gacaagtgtg gggcgtcgta cctctcgtaa ctctaactgg tcttcgacgt cctctagtac | 300 |
| ttcgtctgcc cgatggactg gtagcccccg gtcgcgatgg tccgtctttta gttgctggac | 360 |
| ctcttgaacc cgctctaccc gtcgccgtgg acgccggtcc acaccttcta cgcgaaggcc | 420 |
| ttctggccgg tgcagtaacg gcaattcgtt tacgccgcga ggcccttgtt cctcctcttg | 480 |

-continued

```
ttcgcgtagg agtacctgga cctacaccac gacttctcgg tgctgacggg gatgtagcac    540
gtcacgaaac cctgcaagta gtggttgtgc ctgcagaagt agcggtacct cgagtacccg    600
tggacgcgac tcttcgagtt cttcgcctac gtcccgtggt aggggctcgc gtaagacccg    660
ttctactgtc accgctaaca cttccgcgac atgatggact tcctcttcgt gccacagtag    720
gtggcgctgc agttcgggag gttgtaggac gacctgctcg ccccggtcta gttcgagacg    780
ctgaagccgt agtcgccggc ggaccacctg aggtttcggt tctgcgcctc gcggccgaca    840
cggcggatgt accgtgggct cgcgtaactg ggggtctgg ggtggttcgg cctgatactg    900
taggcccggc tgcatacctc ggacccgtag agcaaccacc tcgaccgttg tcctgtcaaa    960
gggatgttct tgacgttctg cctgaaactc caggagtggt tcaggatgt ccttctcggg    1020 ggcgaagacg ggcctgtgta cccgaagagc cccctgaagg tcaggaagca gtttctgacg    1080
gaatgatttc tagtgtcctt ctctggtttc atattattcg atgaacttgt gtcgaagtag    1140
ttcgcgatgc tctgcgacct ccacctgcac cgcaggacca agttcctaca gtaccgcttc    1200
tgactcagtg gcgcctgatc gccgcaggac tcggtcgggg tggacgggaa gaagtccatc    1260
```

<210> SEQ ID NO 9
<211> LENGTH: 2672
<212> TYPE: DNA
<213> ORGANISM: Homo sapien
<220> FEATURE:
<221> NAME/KEY: misc_feature
<222> LOCATION: (1)...(2672)
<223> OTHER INFORMATION: n = A,T,C or G

<400> SEQUENCE: 9

```
aggccaagaa ttcggcacga ggcttgattt gcatgcaaca cccacaaaaa ggaaacacac    60
cccctcctgc tctggccacc ccagcaggct ccgggggca cctggcctgg gtccccggtg    120
cactcacccg gtccttccca gtcctggacc tcaacgtgga ctgggccagg tgtgggtgag    180
tggagggacg gccaggggca cgatgggagt gaccacctcg cacccccacc ctcagcccgg    240
cccccacccc tgctggagct tgtcacacgt cctcaaaccc ccacatccac tccctctgcc    300
ctccatccct gactccctcc ggaccccctcc cttggccccc gctccgtcac cgattccctc    360
cggtcacctg ctctgcacca tgccccaaga ccaccttccc tgaaggccat cctgtgcggc    420
cagggccccg cagacccctc cacatcccct gaggtcttca actcacccca agctgtggcc    480
cccggagacc ccagagcagc agcccagcc cagctcccca gtgcccgagg gcggttgggg    540
ccccaccaca agcagctaat cgtgactttg gtaaaagttt ctgaaggtac cgacaaccc     600 acgagaacaa gctctcctcc gccccacccc caaacacccc accaagtaca ataaaataca    660
ataaactcca aaaggaccc cctgagatca aagagagaga gagagagaga gagagagcgc    720
gagcgcgcag cccgtccag ccgcagtggc aatgcccaca ctgcctggct gggggccact    780
gactcattgc gccatgggag acctatgcag acccagggga cccgtcagga ggtggctggg    840
cccaggctca ggccagaaga gagacagagg cagggagggt gacgggagag ccagacaagg    900
acagagaggt agagcagggg acagagggcg acggaagagg aacgggcgcg tgggagtggc    960
gaaggacaca gcacgctggg agcgtgcatg gtggctgcgg gactccaggg ctctctcctg    1020
gcccctgggg gccgccccgg cccagaggct gcggctgaat gaacagcgac tctgatcgcg    1080
gcctgctgtc ttccgttcac agtgtctgtc ggggacgca cacggccggc tgaccccggg    1140
gtgggaaggg cgggggggt gggtgggcac cccccactct ctgtcctcag tcctaggtgg    1200
```

-continued

```
ccgtccaggt cccaggtctc ccctggcagg cagctgggtg gccaagtggg gaggggggcc      1260
tgtggccatg cccctggccc cctgtggggc tggccgccgc caagcagcta cctgaagaag      1320
ggcaggtggg gctggctcag gacgccgcta gtccgcggtg actcagtctt cgccatgaca      1380
tccttgaacc aggacgccac gtccacctcc agcgtctcgt agcgcttgat gaagctgtgt      1440
tcaagtagct tattatactt tggtctcttc ctgtgatctt tagtaaggca gtctttgacg      1500
aaggactgga agtcccccga gaagcccatg tgtccgggca gaagcggggg ctcttcctgt      1560
aggactttgg tgaggacctc aaagtccgtc ttgcagttct tgtagggaaa ctgtcctgtt      1620
gccagctcca ccaacgagat gcccaggctc catacgtcgg cccggatgtc atagtccggc      1680
ttggtggggt ctgggggggtc aatgcgctcg ggtgccatga ggcggcacag ccggccgctc     1740
cgcgtcttgg ctttggagtc caccangcgg ccgctgatgc cgaagtcgca gagcttgatc     1800
tggccccgct cgtccagcag gatgttggag ggcttgacgt cgcggtggat gacaccgtgc     1860
ttctccttca ggtagtacag cgccttcaca atcgccactg tcatcttgcc cagaatgcgc     1920
tcggggatgg ggccctgcat ccgcttcttg agcttctcag cgcaggtgcc catgagctcc     1980
atggcgatga agacgtccgt gttggtgatg aacgtcccaa agcactgcac gatgtagggg     2040
cagtcgtggc tcttcagcac cacatccagg tccatgagga tgcgcttgtt ctcctccttg     2100
ttcccggagc gccgcatttg cttaacggca atgacgtggc cggtcttccg gaagcgcatc     2160
ttccacacct ggccgcaggt gccgctgccc atctcgccca agttctccag gtcgttgatt     2220
tctgcctggt agcgctggcc cccgatggtc aggtagcccg tctgcttcat gatctcctgc     2280
agcttctggt caatctcaat gctctccatg ctgcggggtg tgaacagggt tgacgggagc     2340
cccagcatgt ggcggggccg ggcgggggggc gtggggtgct gcggggagct ctctgaggat     2400
ggcgagcggc tgcccccatc gttggccagc gggagctgca gggtgggcct gggccgctgg     2460
gggctgatat ccaggttgag gtcgatcctc cgccgggcct cccggttctc ctgcttcagc     2520
tttgcttcca ggcgggacag cttctgttcc agggaggacg ccgccatctt ccccgccgcc     2580
accgccgccg cgcaccgccc ggccgcccgt cagtccggca gacaaacacc tcgtgccgaa     2640
ttcttggcct cgagggccaa attccctata gt                                   2672
```